US009399672B2

(12) United States Patent
Duan et al.

(10) Patent No.: US 9,399,672 B2
(45) Date of Patent: Jul. 26, 2016

(54) HEPATITIS C VIRUS NEUTRALIZING ANTIBODY

(71) Applicant: The United States of America, as Represented by the Secretary, Department of Health and Human Services, Bethesda, MD (US)

(72) Inventors: Hongying Duan, Arlington, VA (US); Stephen M. Feinstone, Washington, DC (US); Marian Major, Alexandria, VA (US); Pei Zhang, Rockville, MD (US)

(73) Assignee: THE UNITED STATES OF AMERICA, AS REPRESENTED BY THE SECRETARY DEPARTMENT OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 14/401,648

(22) PCT Filed: May 16, 2013

(86) PCT No.: PCT/US2013/041352
§ 371 (c)(1),
(2) Date: Nov. 17, 2014

(87) PCT Pub. No.: WO2013/173582
PCT Pub. Date: Nov. 21, 2013

(65) Prior Publication Data

US 2015/0118242 A1 Apr. 30, 2015

Related U.S. Application Data

(60) Provisional application No. 61/648,386, filed on May 17, 2012.

(51) Int. Cl.

| | |
|---|---|
| ***C07K 16/10*** | (2006.01) |
| ***G01N 33/569*** | (2006.01) |
| ***G01N 33/576*** | (2006.01) |
| *A61K 39/00* | (2006.01) |

(52) U.S. Cl.
CPC ........ *C07K 16/109* (2013.01); *G01N 33/56983* (2013.01); *G01N 33/5767* (2013.01); *A61K 2039/505* (2013.01); *C07K 2317/33* (2013.01); *C07K 2317/34* (2013.01); *C07K 2317/565* (2013.01); *C07K 2317/76* (2013.01); *G01N 2333/186* (2013.01)

(58) Field of Classification Search
None
See application file for complete search history.

(56) References Cited

U.S. PATENT DOCUMENTS

| | | | |
|---|---|---|---|
| 5,053,224 | A | 10/1991 | Koprowski et al. |
| 6,469,143 | B2 | 10/2002 | Sallberg |
| 6,933,366 | B2 | 8/2005 | Sallberg et al. |

(Continued)

OTHER PUBLICATIONS

Bowie et al. Deciphering the Message in Protein Sequences: Tolerance to Amino Acid Substitutions. Science, 1990; 247(4948): 1306-10.*

(Continued)

*Primary Examiner* — Daniel E Kolker
*Assistant Examiner* — Stuart W Snyder
(74) *Attorney, Agent, or Firm* — Cantor Colburn LLP

(57) ABSTRACT

A specific epitope on the surface of the hepatitis C virus that induces a neutralizing antibody response in vivo and neutralizing monoclonal antibodies that bind specifically to the epitope are disclosed. The antibodies block hepatitis C virus from infecting cells.

14 Claims, 7 Drawing Sheets

(56) References Cited

U.S. PATENT DOCUMENTS

| | | | |
|---|---|---|---|
| 7,019,111 | B2 | 3/2006 | Sallberg |
| 7,318,926 | B2 | 1/2008 | Sallberg |
| 8,603,468 | B2 | 12/2013 | Zhang et al. |

OTHER PUBLICATIONS

Bartosch, et al.; "In Vitro Assay for Neutralizing Antibody to Hepatitis C Virus: Evidence for Broadly Conserved Neutralization Epitopes"; Proc Natl Acad Sci USA; 100; pp. 14199-14204; ( 2003).

Brown, et al.; Cross-Genotype Characterization of Genetic Diversity and Molecular Adaptation in Hepatitis C Virus Envelope Glycoprotein Genes; J Gen Virol; 88; pp. 458-469; (2007).

Clayton, et al.; "Analysis of Antigenicity and Topology of E2 Glycoprotein Present on Recombinant Hepatitis C Virus-Like Particles"; J Virol; 76; pp. 7672-7682; (2002).

Deng et al.; "Structural Evidence for a Bifurcated Mode of Action in the Antibody-mediated Neutralization of Hepatitis C Virus"; Proc Natl Acad Sci USA; 110(18); pp. 7418-7422; (2013).

Duan et al.; "Amino Acid Residue-Specific Neutralization and Non-neutralization of Hepatitis C Virus by Monoclonal Antibodies to the E2 Protein"; Journal of Virology; 86(23); pp. 12686-12694; (2012).

Eren, et al.; "Preclinical Evaluation of Two Neutralizing Human Monoclonal Antibodies Against Hepatitis C Virus (HCV): a Potential Treatment to Prevent HCV Reinfection in Liver Transplant Patients"; J Virol; 80; pp. 2654-2664; (2006).

Farci et al.; "Prevention of Hepatitis C Virus Infection in Chimpanzees by Hyperimmmune Serum Against the Hypervariable Region 1 of the Envelope 2 Protein"; Proc Natl Acad Sci USA; 93; pp. 15394-15399; (1996).

Flint,et al.; "Characterization of Hepatitis C Virus E2 Glycoprotein Interaction with a Putative Cellular Receptor, CD81"; J Virol; 73; pp. 6235-6244; (1999).

Hsu et al.; "Hepatitis C Virus Glycoproteins Mediate pH-dependent Cell Entry of Pseudotyped Retroviral Particles"; Proc Natl Acad Sci USA; 100(12); pp. 7271-7276; (2003).

International Search Report and Written Opinion; International Application No. PCT/US2013/041352; International Filing Date May 16, 2013; Date of Mailing Aug. 27, 2013; Applicant's File Reference NIH0065PCT; 13 pages.

Krey et al.; "Structural Basis of HCV Neutralization by Human Monoclonal Antibodies Resistant to Viral Neutralization Escape"; PLOS Pathogens; 9(5); p e1003364; 10 pages; (2013).

Law, et al.; "Broadly Neutralizing Antibodies Protect Against Hepatitis C Virus Quasispecies Challenge"; Nature Medicine; 14; pp. 25-27; 2008.

Logvinoff, et al.; Neutralizing Antibody Response During Acute and Chronic Hepatitis C Virus Infection; Proc Natl Acad Sci USA; 101; pp. 10149-10154; (2004).

Meunier, et al.; "Evidence for Cross-Genotype Neutralization of Hepatitis C Virus Pseudo-Particles and Enhancement of Infectivity by Apolipoprotein C1"; Proc Natl Acad Sci USA; 102; pp. 4560-4565; (2005).

Naicker et al.; Design and Synthesis of aGal-conjugated Peptide T20 as Novel Antiviral Agent for HIV-immunotargeting. Org. Biomol. Chem.; 2; pp. 660-664; (2004).

Owsianka, et al.; "Functional Analysis of Hepatitis C Virus E2 Glycoproteins and Virus-Like Particles Reveals Structural Dissimilarities Between Different Forms of E2"; J Gen Virol; 82; pp. 1877-1883; (2001).

Owsianka, et al.; "Identification of Conserved Residues in the E2 Envelope Glycoprotein of the Hepatitis C Virus That Are Critical for CD81 Binding"; J Virol; 80; pp. 8695-8704; (2006).

Owsianka, et al.; "Monoclonal Antibody AP33 Defines a Broadly Neutralizing Epitope on the Hepatitis C Virus E2 Envelope Glycoprotein"; J Virol; 79; pp. 11095-11104; (2005).

Perotti, et al.; "Identification of a Broadly Cross-Reacting and Neutralizing Human Monoclonal Antibody Directed Against the Hepatitis C Virus E2 Protein"; J Virol; 82; pp. 1047-1052; (2008).

Schofield, et al.; "Human Monoclonal Antibodies That React With the E2 Glycoprotein of Hepatitis C Virus and Possess Neutralizing Activity"; Hepatology; 42; pp. 1055-1062; (2005).

Tarr et al.; "Naturally Occurring Antibodies That Recognize Linear Epitopes in the Amino Terminus of the Hepatitis C Virus E2 Protein C onfer Noninterfering, Additive Neutralization"; Journal of Virology; 86(5); pp. 2739-2749; (2011).

Tarr, et al.; "Characterization of the Hepatitis C Virus E2 Epitope Defined by the Broadly Neutralizing Monoclonal Antibody AP33"; Hepatology; 43; pp. 592-601; (2006).

Tarr, et al.; "Determination of the Human Antibody Response to the Epitope Defined by the Hepatitis C Virus-Neutralizing Monoclonal Antibody AP33"; J Gen Virol; 88; pp. 2991-3001; (2007).

Triyatni, et al.; "Structural Features of Envelope Proteins on Hepatitis C Virus-like Particles as Determined by Anti-envelope Monoclonal Antibodies and CD81 Binding"; Virology; 298; pp. 124-132; (2002).

Yu, et al.; "Neutralizing Antibodies to Hepatitis C Virus (HCV) in Immune Globulins Derived from Anti-HCV-Positive Plastma"; Proc Natl Acad Sci USA; 101; pp. 7705-7710; (2004).

Zeisel, et al.; "Neutralizing Antibodies in Hepatitis C Virus Infection"; World Journal of Gastroenterology; 13; pp. 4824-4830; (2007).

Zhang et al.; "Depletion of Interfering Antibodies in Chronic Hepatitis C Patients and Vaccinated Chimpanzees Reveals Broad Cross-Genotype Neutralizing Activity"; Proc Natl Acad Sci USA; 105(18); pp. 7537-7541; (2009).

Zhang et al.; "Hepatitis C Virus Epitope-Specific Neutralizing Antibodies in IGS Prepared from Human Plasma"; Proc Natl Acad Sci USA; 104(20); pp. 8449-8454; (2007).

Zhen-Yong Keck et al.; "Human Monoclonal Antibodies to the Novel Cluster of Confrmational Epitopes on HCV E2 with Resistance to Neutralization Escape in a Genotype 2a Isolate"; PLOS Pathogens; 8(4); p e1002653; 12 pages; (2012).

* cited by examiner

FIG. 1A
| | | Epitope I | Epitope II | |
|---|---|---|---|---|
| Peptide A | 412 | QLLINTNGSWHINSTA | LNCNESLNTGWLAGLFYQHKF | 447 |
| Peptide B | 427 | | LNCNESLNTGWLAGLFYQHK | 446 |
| B short | 434 | | NTGWLAGLFYQHK | 446 |
| Peptide D | 412 | QLLINTNGSWHINSTA | | 426 |
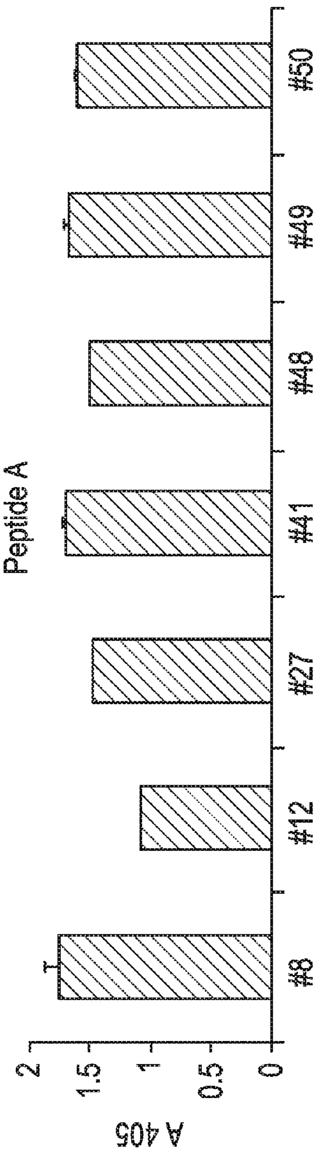
FIG. 1B
Peptide A
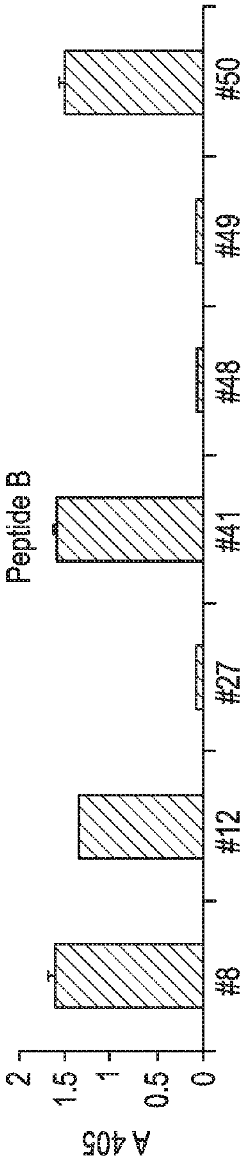
FIG. 1C
Peptide B ID50 neutralization titer

| Neutralizing Antibody | |
|---|---|
| #41 | |
| TWLNMFS | (1/6) |
| SWLDFTH | (1/6) |
| AGPDSWLQWLAQ | (1/6) |
| ITRHSQEWLLEI | (1/6) |
| NGWLMQNTLEPL | (1/6) |
| SQNWLSNMFSYS | (1/6) |
| Core WL X | |
| #8 | |
| WPSPLYE | (8/10) |
| WPTLLYEGPVIR | (2/10) |
| Core WP L | |

```
B short 434NTGWLAGLFYQHK446
W437A      ---A---------
L438A      ----A--------
G440A      ------A------
L441A      -------A-----
F442A      --------A----
```

FIG. 6A

Residues in the E2 protein involved in antibody specific binding

| Residue | Neutralizing Antibody | | Non-neutralizing Antibody | |
|---|---|---|---|---|
| | #8 | #41 | #50 | #12* |
| 437 | + | + | + | + |
| 438 | + | + | + | + |
| 441 | - | - | + | + |
| 442 | - | - | + | - |

+ Contact residue
- Residue little affected by ala substitution
* Non-neutralizing antibody with interfering property

FIG. 6B

```
1a(H77)  412 QLINTNGSWHINSTALNCNESLNTGWLAGLFYQHK 446
1b           --V---------R------D-----F--A---VRN
2a           ------------R------D-----FI-S---T-S
2b           S-----------R------D--Q--F--S---VNN
3a           E-----------R--------I---F------Y--
4            ----S-------R------D-----F------HYS
5            -V----------R-----QD--Q--FI---L-FN-
6            ------------R------D--Q--FI-S---FN-
```

| | | | | |
|---|---|---|---|---|
| Peptide B | 427 | LNCNESLNTGWLAGLFYQHK | 446 |
| B short | 434 | NTGWLAGLFYQHK | 446 |
| W437F | | ---F--------- | |
| W437A | | ---A--------- | |

FIG. 8

```
#41 Kappa
<--------------------------------------------  FR1 - IMGT---------------------
 1              5                   10                  15                 20
 D   V   V   M   T   Q   T   P   L   S   L   P   V   S   L  G   D   Q   A   S
gat gtt gtg atg acc caa act cca ctc tcc ctg cct gtc agt ctt gga gat caa gcc tcc
---------------------->  ___________________CDR1 - IMGT  _____________<-----
                25                  30                  35                  40
I   S   C   R   S   S   Q   N   I   V   H   R       N   G   N   T   Y   L   E
atc tct tgc aga tct agt cag aac att gta cat aga ... aat gga aac acc tat tta gaa
<-------------------------- FR2 - IMGT--------------------->_____________ CDR2
                45                  50                  55                 60
 W   Y   L   Q   K  P   G   Q   S   P   K   L   L   I   Y   K   V
tgg tac ctg cag aaa cca ggc cag tct cca aag ctc ctg atc tac aaa gtt ... ... ...
- IMGT  __________<------- FR3 - IMGT  --------------------------------
               65                  70                  75                  80
               S   N   R   F   S   G   V   P       D   R  F   S   G   S   G
... ... ... ..tcc aac cga ttt tct ggg gtc cca ... gac agg ttc agt ggc agt gga ...
----------------------------------------FR3 - IMGT ----------------------------
           85                  90                  95                100
   S   G   T   D   F   T   L   K   I   S   R   V   E   A   E   D   L   G  L   Y
...tca ggg aca gat ttc aca ctc aag atc agc aga gtg gag gct gag gat ctg gga ctt tat
-------_______CDR3 - IMGT _______________
    104
 Y   C   F   Q   G   S   H   F   P   P   T
tac tgc ttt caa ggt tca cat ttt cct ccc acg
#41 Heavy chain
<--------------------------------------------  FR1 - IMGT---------------------
 1              5                   10                  15                 20
 *   V   K   L   Q   E   S   G   P       E   L   V   K   P  G   A   S   V   K
tag gtg aag ctg cag gag tca gga cct ... gag ctg gtg aag cct ggg gct tca gtg aag
---------------------->  ___________________CDR1 - IMGT  _____________<-----
                25                  30                  35                 40
I  S   C   K   A   S   G   Y   S   F                   T   N   Y   Y   I   N
ata tcc tgc aag gct tct ggc tac agt ttc ... ... ... ... aca aac tac tat ata aat
<------------------------------ FR2 - IMGT------------------------>________ CDR2____
                45                  50                  55                 60
 W   V   K   Q   R   P   G   Q   G   L   E   W   I   G   W   I   F   P   G
tgg gtg aag cag agg cct gga cag gga ctt gag tgg att gga tgg att ttt cct gga ...
- IMGT  __________<-------- FR3 - IMGT  --------------------------------
                65                  70                  75                 80
    G   G   N   T   K   Y   S   E   K   F   K       D   K   A   T   V   T   A
... ggt ggt aat act aag tac agt gag aag ttc aag ... gac aag gcc aca gtc acg gca
------------- FR3 - IMGT ----------------------------------------------------
                85                  90                  95                100
 D   T   S   S   S   T   A   Y   M   Q   L   S   G   L   T   S   E   D   S   A
gac aca tcc tcc agc aca gcc tac atg cag ctc agc ggc ctg aca tct gag gac tct gca
--------------->________________CDR3 - IMGT ______________
           104
 V   Y   F   C   S   R   D   I   Y   G   D   A   W   F   A   Y
gtc tat ttc tgt tca aga gac atc tat ggt gac gcc tgg ttt gct tac
```

HEPATITIS C VIRUS NEUTRALIZING ANTIBODY

CROSS-REFERENCE TO RELATED APPLICATIONS

The present application is a 371 of PCT/US2013/041352 filed May 16, 2013, which claims the benefit of U.S. Provisional Application Ser. No. 61/648,386, filed May 17, 2012, under provisions of 35 U.S.C. 119 and the International Convention for the Protection of Industrial Property, which are incorporated by reference in their entirety.

STATMENT OF GOVERNMENT SUPPORT

This invention was made in part with government support from the National Institutes of Health. The government has certain rights in this invention.

BACKGROUND

Hepatitis C is an infectious disease affecting primarily the liver, caused by the hepatitis C virus (HCV). HCV is a major pathogen transmitted via infected blood that infects some 170 million people around the world. The infection can remain hidden without showing symptoms for years, and many people don't know they are infected.

A feature of HCV is that its course is unpredictable. The virus causes chronic (long-term) infections in 60% to 85% of infected individuals. From 20-50% of these infected individuals develop progressive liver disease, leading ultimately to liver cirrhosis, liver failure and/or hepatocellular carcinoma. Liver damage from chronic hepatitis C virus infection is now the most common cause of liver transplantation in the US. However, a small minority of infected individuals seem to have sufficient immunity that they clear the virus soon after infection.

HCV is a positive-sense RNA virus belonging to the Flaviviridae family. It encodes a single polyprotein of ~3,000 amino acids (aa). Through the action of a combination of host and viral proteases, the polyprotein is cleaved into structural proteins (core, E1, E2, and p'7) and nonstructural proteins (NS2-NS5B). The two envelope glycoproteins, E1 and E2, are believed to form heterodimers/oligomers on the surface of HCV particles that participate in the process of cell entry (Bartosch, B. et al. 2003 J Exp Med 197:633-642).

HCV infection is treated with antiviral medications, e.g. pegylated interferon administered alone or in combination with ribavirin. Combination therapy with pegylated interferon and ribavirin is now successful in about half of the cases, but it is currently prohibitively expensive, requires long-term treatment, and is associated with serious side effects. In much of the world, such treatments are not economically feasible. New direct-acting antiviral drugs such as protease and polymerase inhibitors, either with or without interferon and/or ribavirin, have the potential to increase the response rate and to decrease the duration of treatment. However, these drugs may also have significant side effects and are extremely expensive. Two protease inhibitors are now licensed for use in combination with interferon and ribavirin although the treatment costs are between $26,000-$49,000 per patient depending on the treatment duration, in addition to the costs for pegylated interferon and ribavirin (Tungol, A. et al. J Manag Care Pharm 2011; 17:685-94).

There are at least six known genotypes and more than 50 subtypes of HCV. Specific genotypes are in general located in distinct geographical locations, while a small number of subtypes (1*a*, 1*b*, 2*a* and 3*a*) have recently become more widely distributed and are associated with modern practices such as medical injections, blood products and intravenous drug use. Knowing the genotype can help predict the likelihood of treatment response and, in many cases, determine the duration of treatment. Patients with genotypes 2 and 3 are almost three times more likely than patients with genotype 1 to respond to therapy with alpha interferon or the combination of alpha interferon and ribavirin. When using combination therapy, the recommended duration of treatment depends on the genotype. For patients with genotypes 2 and 3, a 24-week course of combination treatment is adequate, whereas for patients with genotype 1, a 48-week course is recommended Although a vaccine that prevents and treats HCV infection is urgently required, no vaccine is currently available for HCV. A therapeutic vaccine would be an invaluable adjunct to current treatment options for HCV.

One of the major challenges facing the development of treatments or a vaccine for HCV is the high degree of genetic diversity that is exhibited by the virus, estimated to be 10 fold higher than that seen in HIV. Other factors that have hindered vaccine development for HCV include the lack of an accessible animal model and the fact that the virus cannot be easily grown in the laboratory. Although it may not be possible to develop a vaccine that targets all HCV genotypes, genotype specific vaccines that are administered in regions where specific genotypes dominate may be a realistic goal. Both T cell and antibody based vaccines to prevent and also to treat HCV infection are under development.

Further, a major challenge facing HCV infected patients that undergo liver transplants is recurrence of hepatitis C virus infection following otherwise technically successful liver transplantation. Recurrent HCV infection leads to diminished graft and patient survival. Although a number of predictors of severe recurrence have been identified, no definitive strategy has been developed to prevent recurrence. Although hepatitis B virus (HBV)-specific specific antibody products exist that are effective in preventing recurrence of HBV infection in liver transplant patients, no HCV-specific antibody is available yet for preventing recurrence of HCV infection in liver transplant patients. Currently, the only effective treatments for prevention of HCV recurrence after liver transplantation are interferon-based therapies, administered alone or in combination with ribavirin.

There remains a need in the art for more treatments of and vaccines to prevent HCV infection.

SUMMARY

Disclosed herein is an HCV neutralizing antibody binding specifically to HCV E2 protein Epitope II (EPII).

In an embodiment, the antibody or fragment thereof comprises a heavy chain variable region comprising at least one heavy chain complementarity determining region (CDR) amino acid sequence selected from the group consisting of CDR1 comprising residues 25-32 (GYSFTNYY) of SEQ ID NO:2, CDR2 comprising residues 50-57 (IFPGGGNT) of SEQ ID NO:2, and CDR3 comprising residues 96-107 (SRDIY GDAWFAY) of SEQ ID NO:2. In an embodiment, the antibody or fragment thereof comprises a light chain variable region comprising at least one light chain CDR amino acid sequence selected from the group consisting of CDR1 comprising residues 27-37 (QNIVHRNGNTY) of SEQ ID NO:3, CDR2 comprising residues 55-57 (KVS) of SEQ ID NO:3, and CDR3 comprising residues 94-102 (FQGSHFPPT) of SEQ ID NO:3.

In an embodiment, the antibody or fragment thereof comprises a heavy chain variable region comprising a heavy chain third complementarity determining region (CDR3) amino acid sequence comprising residues 96-107 (SRDIYGDAWFAY) of SEQ ID NO:2. In an embodiment, the antibody or fragment thereof comprises a light chain variable region comprising a light chain CDR3 amino acid sequence comprising residues 94-102 (FQGSHFPPT) of SEQ ID NO:3.

In an embodiment, the antibody or fragment thereof binds specifically to hepatitis C virus (HCV) E2 protein Epitope II (EP II), and comprises a heavy chain variable region comprising an amino acid sequence consisting of SEQ ID NO:2 or a light chain variable region comprising an amino acid sequence consisting of SEQ ID NO:3.

In an embodiment, the isolated antibody or a fragment thereof binding specifically to hepatitis C virus (HCV) E2 protein Epitope II (EP II) comprises a heavy chain encoded by a polynucleotide consisting of SEQ ID NO: 4; and a light chain encoded by a polynucleotide consisting of SEQ ID NO: 5.

Compositions comprising the antibody or fragment thereof and methods of making and using the antibody or fragment thereof are also disclosed.

In an embodiment, a method of detecting HCV E2 protein Epitope II comprises contacting the antibody or fragment thereof with a sample under conditions such that the antibody binds an HCV E2 protein Epitope II (EP II) sequence comprising at least residues 434-446 of SEQ ID NO:1; and detecting antibody bound to EP II.

In an embodiment, a method of preventing HCV infection comprises contacting the antibody or fragment thereof to a cell that will be exposed to or infected with HCV.

In an embodiment, a method of treating or preventing HCV infection comprises administering the antibody or fragment thereof to a to a subject exposed to or infected with HCV Hybridomas, polynucleotides encoding the antibody or fragment thereof, recombinant vectors, and host cells expressing the antibody or fragment thereof are also disclosed.

These and other advantages of the invention, as well as additional inventive features, will be apparent from the description of the invention provided herein.

BRIEF DESCRIPTION OF THE DRAWINGS

FIG. 1 presents peptide sequences and histograms showing peptide-specificity of the monoclonal antibodies. Panel (A) presents the amino acid sequences of peptides used in the study. The sequence of Peptide A corresponds to amino acid residues 412-447 of the HCV polyprotein within the region of the E2 protein of HCV H strain (H77, genotype 1*a*) (residues 412-447 of SEQ ID NO:1) and was used to immunize mice to generate the monoclonal antibodies tested in this study. The sequences of truncated forms of Peptide A, i.e., Peptide B, B short and Peptide D are also shown (the indicated residue numbers for each sequence identify the relative position of the sequence in SEQ ID NO:1). The locations of Epitope I and Epitope II within Peptide A are also shown. Panel (B) is a histogram showing Peptide A-specificity of the monoclonal antibodies in an ELISA. The y axis indicates absorbance at 405 nm obtained in the ELISA, representing specific binding of a given antibody to Peptide A. Panel (C) is a histogram showing Peptide B-specificity of the monoclonal antibodies in an ELISA.

FIG. 6A presents a summary of the E2 protein amino acid residues involved in binding of each antibody disclosed herein. FIG. 6B shows the sequence of the HCV 1*a* (H77) genotype from residues 412-447 of SEQ ID NO:1 and summarizes the alignment of amino acid sequences of the E2 region 412-447 of various HCV genotypes below the sequence. Residues identified as involved in binding of the four antibodies disclosed herein are shown in the H77 sequence in bold and underlined letters. In the alignments, a hyphen indicates an amino acid residue identical to that of the H77 sequence.

FIG. 8 shows the nucleic acid sequence (SEQ ID NO: 5) and translated protein sequence (SEQ ID NO: 3) of the kappa chain of antibody #41 and the nucleic acid sequence (SEQ ID NO: 4) and translated protein sequence (SEQ ID NO: 2) of the heavy chain of antibody #41.

DETAILED DESCRIPTION

Figure 2A:
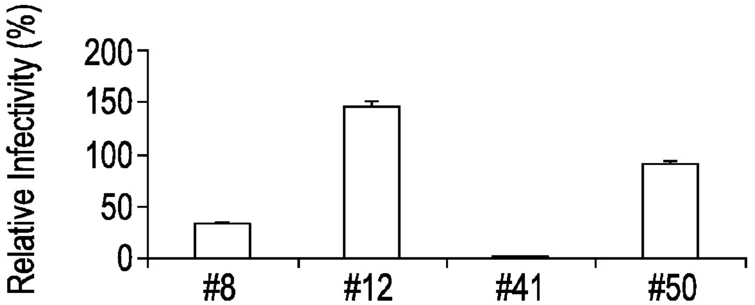
FIG. 2 presents histograms showing neutralization of chimeric viruses by monoclonal antibodies in Huh 7.5 cells. Panel (A) is a histogram showing neutralization of genotype 1*a*/2*a* virus in which the x axis indicates the particular antibody tested in the experiment and the y axis indicates the relative infectivity of the virus (%), i.e., percent of the negative control (cell culture medium). Panel (B) presents histograms showing Peptide B-specific neutralization of genotype 1*a*/2*a* virus by antibody #41. Antibody #41 was adsorbed with (+) or without (−) Peptide B prior to performing an ELISA to test its binding to Peptide B (left panel), and a neutralization assay to assess its neutralizing activity in Huh 7.5 cells (right panel). Each of these samples shown on the x axis was tested at the dilution of 1:$10^5$ in an ELISA. The y axis indicates the absorbance at 405 nm obtained in an ELISA, representing the specific binding of a given antibody to Peptide B. The data shown represent at least 3 independent experiments, with the error bars indicating the standard error of the mean. For the neutralization assay (right panel), the supernatant was diluted at 1:400, and incubated with the genotype 1*a*/2*a* virus before adding the mixture to Huh 7.5 cells. The cell culture medium (Med) was used as the negative control against the tested antibodies. The x axis indicates the samples tested in this assay. The y axis indicates the relative infectivity of the virus (%), i.e., percent of the negative control. The statistical significance of the difference in infectivity is also indicated. Panel (C) is a histogram showing the inability of the antibodies to cross-neutralize the J6/JFH1 virus, a genotype 2*a* virus.

Novel monoclonal antibodies that bind to HCV E2 protein Epitope II (HCV EPII) and inhibit HCV infection of cells are provided herein. In particular, the antibodies described herein are capable of neutralizing HCV genotype 1*a* infectivity in a cell culture system. Therefore, the antibodies of the present invention are useful for treating or preventing HCV infection.

In an embodiment, the isolated neutralizing antibody disclosed herein specifically binds HCV EPII. The antibody can be a monoclonal antibody. The antibody can be an intact antibody or an antigen-binding fragment of the antibody. The antibody can be a mouse, a goat, a sheep, a guinea pig, a rat, or a rabbit antibody. In some embodiments, the antibody can be a rodent antibody, specifically a mouse antibody. The antibody can be a chimeric antibody, specifically a humanized antibody. The HCV EPII epitope recognized can be the HCV 1*a* genotype EPII, comprising $W^{437}$. In some embodiments, the HCV 1*a* genotype EPII recognized comprises $W^{437}$ and $L^{438}$ In an embodiment, the neutralizing antibody comprises a heavy chain variable region amino acid sequence comprising SEQ ID NO:2. In an embodiment, the heavy chain variable region amino acid sequence is SEQ ID NO:2.

In an embodiment, the neutralizing antibody comprises a light (kappa) chain variable region amino acid sequence comprising SEQ ID NO:3. In an embodiment, the light chain variable region amino acid sequence is SEQ ID NO:3.

In an embodiment, the neutralizing antibody comprises a heavy chain variable region encoded by SEQ ID NO:4. In an embodiment, the neutralizing antibody comprises a light (kappa) chain variable region encoded by SEQ ID NO:5.

The isolated neutralizing antibody or antigen-binding fragment thereof can comprise a heavy chain variable region comprising at least one heavy chain complementarity determining region (CDR) amino acid sequence selected from the group consisting of residues 25-32 (GYSFTNYY) of SEQ ID NO:2, 50-57 (IFPGGGNT) of SEQ ID NO:2, and 96-107 (SRDIY GDAWFAY) of SEQ ID NO:2. In an embodiment, the heavy chain variable region comprises CDR amino acid sequences consisting of residues 25-32 (GYSFTNYY) of SEQ ID NO:2, 50-57 (IFPGGGNT) of SEQ ID NO:2, and 96-107 (SRDIY GDAWFAY) of SEQ ID NO:2.

The isolated neutralizing antibody or antigen-binding fragment thereof can comprise a heavy chain variable region comprising a light chain variable region comprising at least one light chain CDR amino acid sequence selected from the group consisting of residues 27-37 (QNIVHRNGNTY) of SEQ ID NO:3, CDR2 comprising residues 55-57 (KVS) of SEQ ID NO:3, and CDR3 comprising residues 94-102 (FQGSHFPPT) of SEQ ID NO:3. In an embodiment, the light chain variable region comprises CDR amino acid sequences consisting of residues 27-37 (QNIVHRNGNTY) of SEQ ID NO:3, CDR2 comprising residues 55-57 (KVS) of SEQ ID NO:3, and CDR3 comprising residues 94-102 (FQGSHFPPT) of SEQ ID NO:3.

The term "neutralizing antibody" is an antibody that is capable of keeping an infectious agent, usually a virus, e.g., HCV, from infecting a cell by neutralizing or inhibiting its biological effect, for example by blocking the receptors on the cell or the virus. Neutralization can happen when antibodies bind to specific viral antigens, blocking the pathogen from entering their host cells.

The term "antibody" or "immunoglobulin," as used interchangeably herein, includes whole antibodies and any antigen binding fragment (antigen-binding portion) or single chain cognates thereof. An "antibody" comprises at least one heavy (H) chain and one light (L) chain. In naturally occurring IgGs, for example, these heavy and light chains are inter-connected by disulfide bonds and there are two paired heavy and light chains, these two also inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR) or Joining (J) regions (JH or JL in heavy and light chains respectively). Each $V_H$ and $V_L$ is composed of three CDRs three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (Clq) of the classical complement system.

The term "antigen-binding portion" or "antigen-binding fragment" of an antibody, as used herein, refers to one or more fragments of an antibody that retain the ability to specifically bind to an antigen (e.g., HVC E2 protein EPII). It has been shown that fragments of a full-length antibody can perform the antigen-binding function of an antibody. Examples of binding fragments denoted as an antigen-binding portion or fragment of an antibody include (i) a Fab fragment, a monovalent fragment consisting of the $V_L$, $V_H$, CL and CH1 domains; (ii) a $F(ab')_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb including VH and VL domains; (vi) a dAb fragment (Ward et al. (1989) *Nature* 341, 544-546), which consists of a $V_H$ domain; (vii) a dAb which consists of a VH or a VL domain; and (viii) an isolated complementarity determining region (CDR) or (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions are paired to form monovalent molecules (such a single chain cognate of an immunoglobulin fragment is known as a single chain Fv (scFv). Such single chain antibodies are also intended to be encompassed within the term "antibody fragment" . Antibody fragments are obtained using conventional techniques known to those with skill in the art, and the fragments are screened for utility in the same general manner as are intact antibodies. Antigen-binding fragments can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. In some embodiments, the term "monoclonal antibody" refers to an antibody derived from a single cell clone. Antigen binding fragments (including scFvs) of such immunoglobulins are also encompassed by the term "monoclonal antibody" as used herein. Monoclonal antibodies are highly specific, being directed against a single antigenic site. Furthermore, in contrast to conventional (polyclonal) antibody preparations, which typically include different antibodies, directed against different determinants (epitopes), each monoclonal antibody is directed against a single epitope on the antigen. Monoclonal antibodies can be prepared using any art recognized technique and those described herein such as, for example, a hybridoma method, a transgenic animal, recombinant DNA methods (see, e.g., U.S. Pat. No. 4,816, 567), or using phage antibody libraries using the techniques described in, for example, US Patent No. 7,388,088 and US patent application Ser. No. 09/856,907 (PCT Int. Pub. No. WO 00/31246). Monoclonal antibodies include chimeric antibodies, human antibodies and humanized antibodies and may occur naturally or be produced recombinantly.The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "chimeric immunoglobulin" or antibody refers to an immunoglobulin or antibody whose variable regions derive from a first species and whose constant regions derive from a second species. Chimeric immunoglobulins or antibodies can be constructed, for example by genetic engineering, from immunoglobulin gene segments belonging to different species.

The term "human antibody," as used herein, is intended to include antibodies having variable regions in which both the framework and CDR regions are derived from human germline immunoglobulin sequences as described, for example, by Kabat et al. (See Kabat, et al. (1991) *Sequences of proteins of Immunological Interest, Fifth Edition*, U.S. Department of Health and Human Services, NIH Publication No. 91-3242). Furthermore, if the antibody contains a constant region, the constant region also is derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The human antibody can have at least one or more amino acids replaced with an amino acid residue, e.g., an activity enhancing amino acid residue that is not encoded by the human germline immunoglobulin sequence. Typically, the human antibody can have up to twenty positions replaced with amino acid residues that are not part of the human germline immunoglobulin sequence. In a particular embodiment, these replacements are within the CDR regions as described in detail below.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, two CDRs, or three CDRs) substantially from a non-human immunoglobulin or antibody, and further includes constant regions (e.g., one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

A non-human antibody is humanized using a method known in the art. In general, a humanized antibody has at least one amino acid residue introduced from a non-human donor. The humanization of a non-human antibody may be performed by replacing CDR sequences of a human antibody with corresponding CDR sequences of a non-human species, e.g., a rodent such as a mouse, having the desired specificity and affinity. Thus, a humanized antibody is a chimeric antibody, and a region that is smaller than the variable region of a substantially intact human antibody may be replaced by the corresponding sequences from a non-human antibody. For example, a humanized antibody may be a human antibody in which some CDR residues and possibly some framework (FR) residues are replaced by residues from the analogous CDR and FR sites in antibodies of a rodent.

An "antigen" is an entity (e.g., a proteinaceous entity or peptide) to which an antibody binds. In various embodiments disclosed herein, an antigen is a peptide derived from the HCV E2 protein comprising Epitope II ("HCV EPII") (a.a. 427-446 of the HCV polyprotein). For example, the antigen can be HCV E2 protein or a peptide comprising aa 427-446 of SEQ ID NO:1, such as Peptide A (FIG. 1A). In some embodiments, an antigen is HCV EPII Peptide B, or Peptide "B short" (FIG. 1A).

The term "epitope" or "antigenic determinant" refers to a site on an antigen to which an immunoglobulin or antibody specifically binds. Epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids, often contiguous amino acids, in a unique spatial conformation. An epitope herein is not limited to a polypeptide having the exact sequence of the portion of the parent protein from which it is derived. Thus the term "epitope" encompasses sequences identical to the native sequence, as well as modifications to the native sequence, such as deletions, additions and substitutions (generally conservative in nature) to which the antibody dislosed herein specifically binds. Methods for determining what epitopes are bound by a given antibody (i.e., epitope mapping) are well known in the art and include, for example, immunoblotting and immunoprecipitation assays, wherein overlapping or contiguous peptides from the antigen are tested for reactivity with the given antibody. The neutralizing monoclonal antibodies disclosed herein bind specifically to HCV EPII.

Methods of determining spatial conformation of epitopes are also well known in the art and include, for example, x-ray crystallography and 2- or more dimensional nuclear magnetic resonance.

The terms "specific binding," "specifically binds," "selective binding," and "selectively binds" mean that an antibody exhibits appreciable affinity for a particular antigen or epitope and, generally, does not exhibit significant cross-reactivity with other antigens and epitopes. "Appreciable" binding affinity includes binding with an affinity of at least $10^6$ $M^{-1}$, specifically at least $10^7$ $M^{-1}$, more specifically at least $10^8$ $M^{-1}$, yet more specifically at least $10^9$ $M^{-1}$, or even yet more specifically at least $10^{1o}$ $M^{-1}$. A binding affinity can also be indicated as a range of affinities, for example, $10^6$ $M^{-1}$ to $10^{1o}$ $M^{-1}$, specifically $10^7$ $M^{-1}$ to $10^{10}$ $M^{-1}$, more specifically $10^8$ $M^{-1}$ to $10^{10}$ $M^{-1}$. An antibody that "does not exhibit significant crossreactivity" is one that will not appreciably bind to an undesirable entity (e.g., an undesirable proteinaceous entity). An antibody specific for a particular epitope will, for example, not significantly crossreact with other epitopes on the same protein or peptide. Specific binding can be determined according to any art-recognized means for determining such binding. In some embodiments, specific binding is determined according to Scatchard analysis and/or competitive binding assays.

The term "linked" used herein refers to a linkage of two entities, for example a labeling material and an antibody, by covalent or non-covalent bonding. A linkage mediated by a linker molecule or the like is also included.

The term "toxic material" used herein refers to a material which can be linked to an antibody or a fragment thereof and can exert toxic effects on a target, such as a cancer cell. For example, radioactive materials such as yttrium-90, iodine-131, etc. and cytotoxic materials such as calicheamicin are included among toxic materials.

The term "labeling material" used herein refers to a material which binds to an antibody or a fragment thereof and is detectable by a physical or chemical method to permit identification of the location or quantity of the antibody or the fragment thereof. The labeling material is used to label the antibody to make detection of bound or unbound antibody easy. Suitable detectable materials include a variety of enzymes, prosthetic groups, fluorescent materials, light-emitting materials and radioactive materials. Examples of suitable enzymes include horseradish peroxidase, alkaline phosphatase, β-galactosidase or acetylcholinesterase. Examples of suitable prosthetic groups include streptavidin/biotin and avidin/biotin. Examples of suitable fluorescent materials include umbelliferone, fluorescein, fluorescein isothiocyanate, rhodamine, dichlorotriazinylamine fluorescein, dansyl chloride or phycoerythrin. Examples of light-emitting materials include luminol, and examples of radioactive materials include 1251, 1311, 35S, and 3H. Detection of the labeling material can be performed by any appropriate method known in the art.

The term "isolated" refers to a nucleic acid, a polypeptide, or other component that is removed from components with which it is naturally associated. The term "isolated" can refer to a polypeptide that is separate and discrete from the whole organism with which the molecule is found in nature or is present in the substantial absence of other biological macromolecules of the same type. The term "isolated" with respect to a polynucleotide can refer to a nucleic acid molecule devoid, in whole or part, of sequences normally associated with it in nature; or a sequence, as it exists in nature, but having heterologous sequences in association therewith; or a molecule disassociated from the chromosome.

The term "isolated nucleic acid molecule" or "isolated polynucleotide" as used herein in reference to nucleic acids encoding antibodies or antibody fragments (e.g., $V_H$, $V_L$, CDR3), is intended to refer to a nucleic acid molecule in which the nucleotide sequences are free of other genomic nucleotide sequences, e.g., those encoding antibodies that bind antigens other than HCV E2 protein EPII, which other sequences may naturally flank the nucleic acid in human genomic DNA.

The term "nucleic acid molecule" or "polynucleotide" as used herein, is intended to include DNA molecules and RNA molecules. A nucleic acid molecule may be single-stranded or double-stranded. A polynucleotide can be obtained by a suitable method known in the art, including isolation from natural sources, chemical synthesis, or enzymatic synthesis.

An isolated polynucleotide encoding an antibody heavy chain variable region having the amino acid sequence of SEQ ID NO: 2 is disclosed. The polynucleotide can comprise SEQ ID NO: 4.

An isolated polynucleotide encoding an antibody light chain variable region having the amino acid sequence of SEQ ID NO: 3. The polynucleotide can comprise SEQ ID NO: 5.

The term "vector" used herein refers to a nucleic acid sequence to express a target gene in a host cell. Examples include a plasmid vector, a cosmid vector, a bacteriophage vector, and a viral vector. Examples of viral vectors include a bacteriophage vector, an adenovirus vector, a retrovirus vector, and an adeno-associated virus vector.

For example, the vector may be an expression vector including a membrane targeting or secretion signaling sequence or a leader sequence, in addition to an expression control element such as promoter, operator, initiation codon, termination codon, polyadenylation signal, and enhancer. The vector may be manufactured in various ways known in the art depending on the purpose. An expression vector may include a selection marker for selecting a host cell containing the vector. Further, a replicable expression vector may include an origin of replication.

The term "recombinant vector" used herein refers to a vector operably linked to a heterologous nucleotide sequence for the purpose of expression, production and isolation of the heterologous nucleotide sequence. The heterologous nucleotide sequence can be a nucleotide sequence encoding all or part of the heavy chain or the light chain of an antibody disclosed herein.

The recombinant vector may be constructed for use in prokaryotic or eukaryotic host cells. For example, when a prokaryotic cell is used as a host cell, the expression vector used generally includes a strong promoter capable of initiating transcription (for example, $p_L^{\lambda}$ promoter, trp promoter, lac promoter, tac promoter, T7 promoter), a ribosome binding site for initiating translation, and a transcription/translation termination sequence. When a eukaryotic cell is used as a host cell, the vector used generally includes the origin of replication acting in the eukaryotic cell, for example f1 origin of replication, SV40 origin of replication, pMB1 origin of replication, adeno origin of replication, AAV origin of replication, or BBV origin of replication, but is not limited thereto. A promoter in an expression vector for a eukaryotic host cell may be a promoter derived from the genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV). A transcription termination sequence in an expression vector for a eukaryotic host cell may be, in general, a polyadenylation sequence.

The term "operably linked" refers to a nucleic acid sequence placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

A single vector can be used to simultaneously express both the heavy chain and the light chain of the antibody. Alternatively, the heavy chain and the light chain of the antibody can be expressed from two different vectors. In the latter case, the two vectors may be introduced into a single host cell by simultaneous transduction or targeted transduction.

The host cell of the vector may be any cell that can be practically utilized by the expression vector. For example, the host cell may be a higher eukaryotic cell, such as a mammalian cell, or a lower eukaryotic cell, such as a yeast cell. Further, the host cell may be a prokaryotic cell, such as a bacterial cell. A prokaryotic host cell may be a *Bacillus* genus bacterium, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*; or an intestinal bacterium, such as *Salmonella typhimurium, Serratia marcescens*, and various *Pseudomonas* species. A eukaryotic host cell may be a yeast (e.g., *Saccharomyces cerevisiae*), an insect ell, a plant cell, or an animal cell, for example, mouse Sp2/0, CHO (Chinese hamster ovary) K1, CHO DG44, PER.C6, W138, BHK, COS-7, 293, HepG2, Huh7, 3T3, RIN, or a MDCK cell line.

The polynucleotide or recombinant vector including the polynucleotide may be transferred into the host cell using a method known in the art. For example, when a prokaryotic cell is used as the host cell, the transfer may be performed using a $CaCl_2$ method or an electroporation method, and when a eukaryotic cell is used as the host cell, the transfer may be performed by microinjection, calcium phosphate precipitation, electroporation, liposome-mediated transfection, or gene bombardment, but is not limited thereto.

Disclosed herein is a recombinant vector comprising a polynucleotide consisting of SEQ ID NO: 4. Also disclosed is a recombinant vector comprising a polynucleotide consisting of SEQ ID NO: 5. A suitable host cell can be transformed with one or both of the recombinant vectors or one or both of the polynucleotides.

A method of isolating the antibody from the host cell is also disclosed. In an embodiment the method comprises culturing the host cell and isolating from the culture an antibody binding to HCV EPII. The method can further comprise screening the antibody in a cell culture system to determine that it is a neutralizing antibody. A genotype 1*a* HCV or a chimeric HCV including gentoype 1*a* EPII can be used in the screening assay to determine if the isolated antibody reduces infectivity of the HCV.

The term "patient" includes human and other mammalian subjects that receive either prophylactic or therapeutic treatment.

As used herein, the term "subject" includes any human or non-human animal. For example, the methods and compositions of the present invention can be used to treat a subject having cancer. In a particular embodiment, the subject is a human. The term "non-human animal" includes all vertebrates, e.g., mammals and non-mammals, such as non-human primates, sheep, dog, cow, chickens, amphibians, reptiles, etc.

The terms "treat", "treating" and "treatment" mean implementation of therapy with the intention of reduction in severity or frequency of symptoms, elimination of symptoms or their underlying cause, prevention of the occurrence of symptoms or their underlying cause, or improvement or remediation of damage.

The term "sample" refers to tissue, body fluid, or a cell from a patient or a subject. Normally, the tissue or cell will be removed from the subject, but in vivo diagnosis is also contemplated.

The term "E2 polypeptide" is intended to refer to a molecule derived from an HCV E2 region. The mature E2 region of HCV-Ia begins at approximately amino acid 384, numbered relative to the full-length HCV-I polyprotein (SEQ ID NO:1). A signal peptide begins at approximately amino acid 364 of the polyprotein. The corresponding region for other HCV genotypes and subtypes are known and readily determined by comparison to the HCV-Ia polyprotein. For ease of discussion then, numbering herein is with reference to the HCV-Ia polyprotein, but it is to be understood that an "E2 polypeptide" also encompasses E2 polypeptides from any of the various HCV genotypes, such as HCV-I, HCV-2, HCV-3, HCV-4, HCV-5 and HCV-6 and subtypes thereof, such as HCV-Ia, HCV-2*a,* HCV-3*a,* HCV-4*a,* HCV-5*a* and HCV-6*a.* Thus, for example, the term "E2" polypeptide refers to native E2 sequences from any of the various HCV genotypes, unless specifically identified, as well as analogs, muteins and immunogenic fragments, as discussed further below. The complete genotypes of many of these strains are known. See, e.g., Simmonds et al. 2005 Hepatology 42:962-973.

Furthermore, an "E2 polypeptide" may not be limited to a polypeptide having the exact sequence depicted in the HCV databases. The HCV genome is in a state of constant flux in vivo and contains several variable domains which exhibit relatively high degrees of variability between isolates. A number of conserved and variable regions are known between these strains and, in general, the amino acid sequences of epitopes derived from these regions will have a high degree of sequence homology, e.g., amino acid sequence homology of more than 30%, preferably more than 40%, more than 60%, and even more than 80-90%, or at least 95% homology or identity, when the two sequences are aligned.

Additionally, the term "E2 polypeptide" may encompass proteins, which include modifications to the native sequence, such as internal deletions, additions and substitutions (generally conservative in nature), such as proteins substantially homologous to the parent sequence. These modifications may be deliberate, as through site-directed mutagenesis, or may be accidental, such as through naturally occurring mutational events. All of these modifications are encompassed in certain embodiments so long as the modified E2 polypeptides function for their intended purpose. Thus, for example, if the E2 polypeptides are to be used in immunogenic compositions, the modifications must be such that immunological activity (i.e., the ability to elicit a humoral or cellular immune response to the polypeptide) is not lost.

"Homology" refers to the percent identity between two polynucleotide or two polypeptide moieties. Two DNA, or two polypeptide sequences are "substantially homologous" to each other when the sequences exhibit at least about 50% , preferably at least about 75%, more preferably at least about 80%-85%, preferably at least about 90%, and most preferably at least about 95%-98% sequence identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353-358, National Biomedical Research Foundation, Washington, D.C., which adapts the local homology algorithm of Smith and Waterman 1981 Advances in Appl Math 2:482-489, for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Alternatively, nucleotide homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., *Sambrook et al. Molecular Cloning: A Laboratory Manual* (2d ed., Cold Spring Harbor Laboratory Press, Cold Spring Harbor, N. Y. (1989).

Tthe term "recombinant" can be used to describe a nucleic acid molecule and refers to a polynucleotide of genomic, RNA, DNA, cDNA, viral, semisynthetic, or synthetic origin which, by virtue of its origin or manipulation is not associated with all or a portion of the polynucleotide with which it is associated in nature. The term "recombinant" as used with respect to a protein or polypeptide can refer to a polypeptide produced by expression of a recombinant polynucleotide. In general, the gene of interest is cloned and then expressed in transformed organisms, as described further below. The host organism expresses the foreign gene to produce the protein under expression conditions.

The terms "analog" and "mutein" can refer to biologically active derivatives of the reference molecule, such as E2 or an immunogenic fragment of E2, or fragments of such derivatives, that retain desired activity, such as immunoreactivity in assays described herein. In general, the term "analog" refers to compounds having a native polypeptide sequence and structure with one or more amino acid additions, substitutions (generally conservative in nature) and/or deletions, relative to the native molecule, so long as the modifications do not destroy immunogenic activity. The term "mutein" refers to polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. Preferably, the analog or mutein has at least the same immunoreactivity as the native molecule. Methods for making polypeptide analogs and muteins are known in the art.

A conservative amino acid substitution in a polypeptide sequence includes the substitution of an amino acid in one class by an amino acid of the same class, where a class is defined by common physicochemical amino acid side chain properties and high substitution frequencies in homologous proteins found in nature, as determined, for example, by a standard Dayhoff frequency exchange matrix or BLOSUM matrix. Six general classes of amino acid side chains have been categorized and include: Class I (Cys); Class II (Ser, Thr, Pro, Ala, Gly); Class III (Asn, Asp, Gln, Glu); Class IV (His, Arg, Lys); Class V (Ile, Leu, Val, Met); and Class VI (Phe, Tyr, Trp). For example, substitution of an Asp for another class III residue such as Asn, Gln, or Glu, is a conservative substitution. One of skill in the art can readily determine regions of the molecule of interest that can tolerate change by reference to Hopp/Woods and Kyte—Doolittle plots. With respect to substitutions in antibodies, methods of identifying nucleotide and amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:.412-417 (1997)).

An "immunogenic fragment" of a particular HCV protein will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, that define an epitope, or any integer between 5 amino acids and the full-length sequence, provided that the fragment in question retains the ability to elicit an immunological response as defined herein.

Monoclonal antibodies of the invention can be produced using a variety of known techniques, such as the standard somatic cell hybridization technique described by Kohler and Milstein (1975) *Nature* 256: 495, viral or oncogenic transformation of B lymphocytes or phage display technique using libraries of human antibody genes. In particular embodiments, the antibodies are humanized monoclonal antibodies.

Accordingly, in one embodiment, a hybridoma method is used for producing an antibody that binds HCV E2 protein EPII ("HCV EPII"). In this method, a mouse or other appropriate host animal can be immunized with a suitable antigen in order to elicit lymphocytes that produce or are capable of producing antibodies that will specifically bind to the antigen used for immunization. In some embodiments, the antigen is Peptide A, Peptide B, or Peptide B-short. Alternatively, lymphocytes may be immunized in vitro. Lymphocytes can then be fused with myeloma cells using a suitable fusing agent, such as polyethylene glycol, to form a hybridoma cell (Goding, Monoclonal Antibodies: Principles and Practice, pp. 59-103 (Academic Press, 1986)). Culture medium in which hybridoma cells are growing is assayed for production of monoclonal antibodies directed against the antigen. After hybridoma cells are identified that produce antibodies of the desired specificity, affinity, and/or activity, the clones may be subcloned by limiting dilution procedures and grown by standard methods (Goding, Monoclonal Antibodies:Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones can be separated from the culture medium, ascites fluid, or serum by conventional immunoglobulin purification procedures such as, for example, protein A-Sepharose, hydroxylapatite chromatography, gel electrophoresis, dialysis, or affinity chromatography.

As discussed further below, a hybridoma cell producing monoclonal antibody #41 and a hybridoma cell producing monoclonal antibody #8 are disclosed herein.

The binding specificity to HCV E2 protein EPII of monoclonal antibodies, or fragments thereof, prepared using any technique including those disclosed herein, can be determined by immunoprecipitation or by an in vitro binding assay, such as radioimmunoassay (RIA) or enzyme-linked immunoabsorbent assay (ELISA). The binding affinity of a monoclonal antibody or portion thereof also can be determined by the Scatchard analysis of Munson et al., Anal. Biochem., 107:220 (1980).

In certain embodiments, an antibody binding HCV E2 protein EPII may be further altered or optimized to achieve a desired binding specificity and/or affinity using art recognized techniques, such as those described herein.

In one embodiment, partial antibody sequences derived from a given antibody may be used to produce structurally and functionally related antibodies. For example, antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences.

Thus, one or more structural features of an anti-HCV EPII antibody disclosed herein, such as the CDRs, can be used to create structurally related anti-HCV EPII antibodies that retain at least one functional property of the antibodies of the invention, e.g., inhibiting infection of cells exposed to HCV.

Antibody heavy and light chain CDR3 domains are known to play a particularly important role in the binding specificity/affinity of an antibody for an antigen. Accordingly, in certain embodiments, antibodies are generated that include the heavy and/or light chain CDR3s of the particular antibodies described herein. The antibodies can further include the heavy and/or light chain CDR1 and/or CDR2s of the antibodies disclosed herein.

The CDR 1, 2, and/or 3 regions of the engineered antibodies described above can comprise the exact amino acid sequence(s) as those disclosed herein. However, the ordinarily skilled artisan will appreciate that some deviation from the exact CDR sequences may be possible, particularly for CDR1 and CDR2 sequences, which can tolerate more variation than CDR3 sequences without altering epitope specificity (such deviations are, e.g., conservative amino acid substitutions). Accordingly, in another embodiment, the engineered antibody may be composed of one or more CDR1s and CDR2s that are, for example, 90%, 95%, 98%, 99% or 99.5% identical to the corresponding CDRs of an antibody named herein.

In another embodiment, one or more residues of a CDR may be altered to modify binding to achieve a more favored on-rate of binding. Using this strategy, an antibody having ultra high binding affinity of, for example, $10^{10}$ $M^{-1}$ or more, can be achieved. Affinity maturation techniques, well known in the art and those described herein, can be used to alter the CDR region(s) followed by screening of the resultant binding molecules for the desired change in binding. Accordingly, as CDR(s) are altered, changes in binding affinity as well as immunogenicity can be monitored and scored such that an antibody optimized for the best combined binding and low immunogenicity are achieved.

Modifications can also be made within one or more of the framework or joining regions of the heavy and/or the light chain variable regions of an antibody, so long as antigen binding affinity subsequent to these modifications is better than $10^6$ $M^{-1}$.

In another embodiment, the antibody is further modified with respect to effector function, so as to enhance the effectiveness of the antibody in treating cancer, for example. For example cysteine residue(s) may be introduced in the Fc region, thereby allowing interchain disulfide bond formation in this region.

In another aspect, a composition, e.g., a pharmaceutical composition, is disclosed herein. The composition can contain one or a combination of monoclonal antibodies, (or antigen-binding fragments thereof), formulated together with a pharmaceutically acceptable carrier. In one embodiment, the composition includes an isolated antibody that binds HCV EPII. In an embodiment, the composition contains an isolated antibody or fragment thereof disclosed herein and at least one additional therapeutic agent. The therapeutic agent can be a small molecule drug, or a biological such as a hormone, a protein, or another antibody or fragment thereof. In some embodiments, the composition further comprises a pharmaceutically acceptable carrier. A "therapeutic agent" means a substance that when administered to a patient provides any therapeutic benefit. A therapeutic benefit may be an amelioration of symptoms of HCV infection or prevention of HCV infection.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, may be coated in a material to protect the compound from the action of acids and other natural conditions that may inactivate the compound.

Compositions can be administered alone or in combination therapy, i.e., combined with other agents. For example, the combination therapy can include a composition provided herein with at least one or more additional therapeutic agents, such as an anti-viral agent described herein, or another antibody.

Compositions can be administered by a variety of methods known in the art. As will be appreciated by the skilled artisan, the route and/or mode of administration will vary depending upon the desired results. The antibodies can be prepared with carriers that will protect the antibodies against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J.R. Robinson, ed., Marcel Dekker, Inc., New York, 1978.

To administer compositions by certain routes of administration, it may be necessary to coat the constituents, e.g., antibodies, with, or co-administer the compositions with, a material to prevent its inactivation. For example, the compositions may be administered to a subject in an appropriate carrier, for example, liposomes, or a diluent. Acceptable diluents include saline and aqueous buffer solutions. Liposomes include water-in-oil-in-water CGF emulsions as well as conventional liposomes (Strejan et al. (1984) J. Neuroimmunol. 7:27).

Acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the antibodies, use thereof in compositions provided herein is contemplated. Supplementary active constituents can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Including in the composition an agent that delays absorption, for example, monostearate salts and gelatin can bring about prolonged absorption of the injectable compositions.

Sterile injectable solutions can be prepared by incorporating the monoclonal antibodies in the required amount in an appropriate solvent with one or a combination of ingredients enumerated above, as required, followed by sterilization microfiltration. Generally, dispersions are prepared by incorporating the antibodies into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, human antibodies may be administered once or twice weekly by subcutaneous injection or once or twice monthly by subcutaneous injection.

It can be advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of antibodies calculated to produce the desired therapeutic effect in association with the required pharmaceutical carrier. The specification for the dosage unit forms provided herein are dictated by and directly dependent on (a) the unique characteristics of the antibodies and the particular therapeutic effect to be achieved, and (b) the limitations inherent in the art of compounding such antibodies for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic compositions, formulations include those suitable for oral, nasal, topical (including buccal and sublingual), rectal, and parenteral administration. Parenteral administration is the most common route of administration for therapeutic compositions comprising antibodies. The formulations may conveniently be presented in unit dosage form and may be prepared by any methods known in the art of pharmacy. The amount of antibodies that can be combined with a carrier material to produce a single dosage form will vary depending upon the subject being treated, and the particular mode of administration. This amount of antibodies will generally be an amount sufficient to produce a therapeutic effect. Generally, out of one hundred per cent, this amount will range from about 0.001 per cent to about ninety percent of antibody by mass, preferably from about 0.005 per cent to about 70 per cent, most preferably from about 0.01 per cent to about 30 per cent.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Examples of suitable aqueous and nonaqueous carriers which may be employed in the pharmaceutical compositions provided herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Particular examples of adjuvants which are well-known in the art include, for example, inorganic adjuvants (such as aluminum salts, e.g., aluminum phosphate and aluminumhydroxide), organic adjuvants (e.g., squalene), oil-based adjuvants, virosomes (e.g., virosomes which contain a membrane-bound heagglutinin and neuraminidase derived from the influenza virus).

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

When compositions are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

Regardless of the route of administration selected, compositions provided herein, may be used in a suitable hydrated form, and they may be formulated into pharmaceutically acceptable dosage forms by conventional methods known to those of skill in the art.

Actual dosage levels of the antibodies in the pharmaceutical compositions provided herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the composition required. For example, the physician or veterinarian could start doses of the antibodies at levels lower than that required to achieve the desired therapeutic effect and gradually increasing the dosage until the desired effect is achieved. In general, a suitable daily dose of compositions provided herein will be that amount of the antibodies which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for antibodies to be administered alone, it is preferable to administer antibodies as a formulation (composition).

Therapeutic compositions can be administered with medical devices known in the art. For example, in a preferred embodiment, a therapeutic composition can be administered with a needleless hypodermic injection device, such as the devices disclosed in U.S. Pat. Nos. 5,399,163, 5,383,851, 5,312,335, 5,064,413, 4,941,880, 4,790,824, or 4,596,556. Examples of well-known implants and modules useful in methods disclosed herein include: U.S. Pat. No. 4,487,603, which discloses an implantable micro-infusion pump for dispensing medication at a controlled rate; U.S. Pat. No. 4.,486,194, which discloses a therapeutic device for administering medications through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the monoclonal antibodies can be formulated to ensure proper distribution in vivo. For example, the therapeutic can be formulated in liposomes. Methods of manufacturing liposomes are known in the art. The liposomes may comprise one or more moieties that are selectively transported into specific cells or organs, thus enhance targeted drug delivery.

Also provided are methods of using antibodies (and antigen binding fragments thereof) that bind HCV EPII in a variety of ex vivo and in vivo diagnostic and therapeutic applications involving HCV.

Accordingly, in one embodiment, the antibody or a fragment thereof specifically binding HCV EPII can be used to detect HCV in a sample. In some embodiments, the antibody or a fragment thereof specifically binding HCV EPII can be used to detect HCV genotype 1*a* in a sample. In an embodiment, the method comprises contacting the antibody or fragment thereof with a sample under conditions such that the antibody binds HCV EPII; and detecting antibody bound to HCV EPII. Such a method could be a component of a diagnostic method for HCV infection or for a method of identifying the genotype of HCV infection, for example to optimize treatment. In one embodiment, a method is provided for treating or preventing HCV infection by administering to a subject an HCV neutralizing antibody disclosed herein. The HCV neutralizing antibody can be administered alone or in combination with one or more additional therapeutic agents. The HCV neutralizing antibody can be administered in an amount effective to treat or prevent HCV infection. In some embodiments, the subject can be a liver transplant patient, specifically the liver transplant patient can have chronic hepatitis C. A "liver transplant patient" is a patient in any stage associated with obtaining a liver transplant, including for example a patient with liver disease evaluated as needing a liver transplant, a patient scheduled for a liver transplant, or a patient post-liver transplant.

The term "effective amount," as used herein, refers to that amount of an antibody or an antigen binding fragment thereof that binds HCV E2 protein EPII, which is sufficient to effect treatment or prevent HCV infection, as described herein, when administered to a subject. Therapeutically effective amounts of antibodies of the present invention will vary depending upon the relative activity of the antibodies (e.g., in inhibiting HCV infection of cells) and depending upon the subject and disease condition being treated, the weight and age of the subject, the severity of the disease condition, the manner of administration and the like, which can readily be determined by one of ordinary skill in the art. The dosages for administration can range from, for example, about 1 ng to about 10,000 mg, about 5 ng to about 9,500 mg, about 10 ng to about 9,000 mg, about 20 ng to about 8,500 mg, about 30 ng to about 7,500 mg, about 40 ng to about 7,000 mg, about 50 ng to about 6,500 mg, about 100 ng to about 6,000 mg, about 200 ng to about 5,500 mg, about 300 ng to about 5,000 mg, about 400 ng to about 4,500 mg, about 500 ng to about 4,000 mg, about 1 μg to about 3,500 mg, about 5 μg to about 3,000 mg, about 10 ,ig to about 2,600 mg, about 20 ,ig to about 2,575 mg, about 30 μg to about 2,550 mg, about 40 ,ig to about 2,500 mg, about 50 ,ig to about 2,475 mg, about 100 μpg to about 2,450 mg, about 200 μg to about 2,425 mg, about 300 μg to about 2,000, about 400 μg to about 1,175 mg, about 500 μg to about 1,150 mg, about 0.5 mg to about 1,125 mg, about 1 mg to about 1,100 mg, about 1.25 mg to about 1,075 mg, about 1.5 mg to about 1,050 mg, about 2.0 mg to about 1,025 mg, about 2.5 mg to about 1,000 mg, about 3.0 mg to about 975 mg, about 3.5 mg to about 950 mg, about 4.0 mg to about 925 mg, about 4.5 mg to about 900 mg, about 5 mg to about 875 mg, about 10 mg to about 850 mg, about 20 mg to about 825 mg, about 30 mg to about 800 mg, about 40 mg to about 775 mg, about 50 mg to about 750 mg, about 100 mg to about 725 mg, about 200 mg to about 700 mg, about 300 mg to about 675 mg, about 400 mg to about 650 mg, about 500 mg, or about 525 mg to about 625 mg, of an antibody or antigen binding portion thereof, according to the invention. Dosage regimens may be adjusted to provide the optimum therapeutic response. An effective amount is also one in which any toxic or detrimental effects (i.e., side effects) of an antibody or antigen binding fragment thereof are minimized and/or outweighed by the beneficial effects.

The antibody can be administered alone or with another therapeutic agent that acts in conjunction with or synergistically with the antibody to treat or prevent HCV infection. Such therapeutic agents include those described herein, for example, small organic molecules, monoclonal antibodies, and recombinantly engineered biologics.

Also provided are kits comprising one or more anti-HCV EPII antibodies (or antigen binding fragments thereof), optionally contained in a single vial, and include, e.g., instructions for use in treating or preventing HCV infection. The kits may include a label indicating the intended use of the contents of the kit. The term label includes any writing, marketing materials or recorded material supplied on or with the kit, or which otherwise accompanies the kit.

Other embodiments of the present invention are described in the following non-limiting Examples.

EXAMPLES

Materials and Methods

Peptide synthesis. All peptides were chemically synthesized by the Core Laboratory of the Center for Biologics Evaluation and Research at the US Food and Drug Administration, with an Applied Biosystems (Foster City, CA) Model 433A peptide synthesizer. Biotinylated peptides were synthesized with Fmoc-Lys (Biotin-LC)-Wang resin (AnaSpec, San Jose, CA) as described previously (Zhang P et al. 2007).

ELISA. Biotin-conjugated peptide (200 ng/well) was added to streptavidin-coated 96-well Maxisorp plates (Pierce) and incubated at room temperature for 1 hour (h) in Super Block Blocking Buffer (Thermo Scientific). The wells were blocked further in blocking buffer for another hour at 37° C. After washing the plate 4× with phosphate buffered saline (PBS) buffer pH 7.4 containing 0.05% Tween-20 to remove unbound peptides, serial dilutions of the test antibodies were added to the plate and incubated at 37° C. for 1 h. The plate was then washed 4× before the secondary monoclonal antibody, either a goat anti-mouse peroxidase-conjugated IgG or a goat anti-human peroxidase-conjugated IgG (Sigma-Aldrich) at a 1:5000 dilution, was added to the wells and incubated at 37° C. for lh. After 4 washes, the reaction was developed with ABTS peroxidase substrate (KPL, Gaithersburg, MD) and stopped by adding 100 μL of a 1% SDS solution, or the reaction was developed with 1-Step TMB-ELISA substrate solution (KPL, Gaithersburg, MD) and stopped by adding 100 μL 4N Sulfuric Acid. The absorbance of each well was measured at 405 nm and 450 nm, respectively, using a SpectraMax M2e microplate reader (Molecular Devices).

Neutralization assay. Virus stocks were prepared by transfecting full-length HCV RNA derived from an HCV genotype 2*a* clone, J6/JFH1 (a gift from Charles Rice, Rockefeller University), into Huh 7.5 cells as previously described (Duan H et al. 2010. Vaccine. 28:4138-4144, Zhang et al. 2007, Zhang P et al. 2009). An HCV genotype 1*a*/2*a* chimera virus was produced by replacing the structural genes of J6/JFH1 with that of the HCV H strain (H77), which is known to be genotype 1*a*. Briefly, Huh 7.5 cells were seeded at a density of 4-5×103 cells/well in 96-well plates to obtain approximately 60% confluence in 24 h. The virus stock was diluted in DMEM supplemented with 10% fetal bovine serum (FBS)/1% penicillin/streptomycin/2 mM glutamine to yield approximately 50 infected foci per well in the absence of antibodies. Viruses were mixed with a diluted antibody or with cell culture medium, incubated at 37° C. for 1 h, and then inoculated into Huh 7.5 cells. After 3 days in culture, virus foci were detected either by immunofluorescence or immunoperoxidase staining and then counted. Neutralization was determined by comparing the infectivity of the viruses incubated with the antibody to the infectivity of the viruses incubated with medium alone or with pre-immune plasma. The median 50% inhibitory dilution (ID5o) was determined according to the method of Reed and Muench (1938. Am. J. Hyg. 27:493-497). Statistical analysis was performed with GraphPad Prism 4 (GraphPad Software, La Jolla, CA) by using the unpaired t-test with two-tailed P value (P value <0.05). Error bars represent the standard deviation or the standard error of the mean.

Enrichment and removal of peptide-specific antibodies. 500 ng of biotinylated Peptide B, Peptide D or an unrelated peptide control (a pool of overlapping peptides representing the M2 protein from the Influenza virus) was mixed with 100 μL of streptavidin-coated Dynabeads (Invitrogen, Grand Island, N.Y.) and incubated at room temperature for 1 h. After washing with PBS (pH 7.4), the beads were mixed with an appropriate dilution of ascites fluid or plasma, which contained specific antibodies, and incubated at room temperature for 1 h. To enrich for peptide-specific antibodies, the beads were collected with a magnet stand. After washing the beads with PBS, the antibodies were eluted from the beads with Glycine-HCl solution (pH 2.2). The eluates were neutralized by mixing with an equal volume of Tris-HCl buffer (pH 9.2). In contrast, to remove the peptide-specific antibodies, the beads were pelleted with a magnet stand and the supernatant was collected for further analysis.

Phage display. The selection of peptides from random peptide phage display libraries (New England Biolabs, Beverly, Mass.) was described previously (Zhang P et al. 2007). Briefly, $10^{10}$ phages were incubated with individual monoclonal antibody/protein G mixtures at room temperature for 20 min. After 8 washes with 0.05 M Tris-HCl buffer (pH 7.5) containing 0.15 M NaCl and 0.05% Tween-20, the phages were eluted from the complexes with 0.1 M HCl and neutralized with 1 M Tris-HCl buffer (pH 9.0). The eluted phages were then amplified in the host strain ER2738 for 4-5 h. After three additional rounds of selection of amplified phages by the same monoclonal antibody, the DNA from each single-phage plaque was sequenced, and the corresponding peptide sequence was then deduced from the DNA sequence.

Statistical analysis: Statistical analysis was performed with GraphPad Prism 4 using unpaired t-test with two-tailed P value (P value<0.05). Error bars represent the standard deviation or the standard error of the mean.

Example 1

Generation of Monoclonal Antibodies

Monoclonal antibodies were produced using the standard procedures of Harlan Bioproducts for Science (Indianapolis, Ind.). Briefly, Balb/c mice were injected intraperitoneally (i.p.) with a chemically synthesized Peptide A (amino acid residues 412-447 of the E2 protein from the HCV H strain (H77) (FIG. 1A), which was conjugated to keyhole limpet hemocyanin (KLH). Mice that produced high titers of antibody to Peptide A were selected for cell fusion to generate hybridomas. Antibody-positive cells were cloned by the limiting dilution method for several cycles. At each cloning cycle, the tissue culture supernatant of each clone was screened by ELISA for the presence of antibodies to Peptide B (Epitope II). The selected anti-Peptide B-positive clones were injected i.p. into Balb/c mice primed with pristane (Sigma-Aldrich) to produce ascites fluid.

A panel of hybridoma cell lines that produced monoclonal antibodies was obtained after immunizing the mice with Peptide A (a.a. 412-447) (FIG. 1A). Using an ELISA, seven monoclonal antibodies (ascites fluid) from the panel that bound to Peptide A were identified (FIG. 1B). Biotin-conjugated Peptide A (200 ng/well) was added to streptavidin-coated 96-well plates. Each monoclonal antibody (ascites fluid) was diluted 1:1000 and used as the primary antibody. The results are shown in FIG. 1B in which the y axis indicates absorbance at 405 nm obtained in the ELISA, representing specific binding of a given antibody to Peptide A. Data shown represent the mean of three independent experiments, with the standard deviation indicated by the error bar extending from the top of each bar.

A similar ELISA was performed to detect specific binding of the panel of antibodies to Peptide B. Biotin-conjugated Peptide B (200 ng/well) was added to the streptavidin-coated 96-well plates. The ELISA conditions were similar to those in the Peptide A-specificity experiment. The data, shown in FIG. 1C, also represent at least 3 independent experiments.

The binding capacity toward Peptide A of the seven antibodies was comparable at a dilution of 1:1000 (FIG. 1B). Four of the seven antibodies, namely, #8, #12, #41 and #50, were also shown to bind specifically to Peptide B (FIG. 1A and C), while the other three antibodies, #27, #48 and #49 did not bind to Peptide B (FIG. 1C).

Example 2

Neutralization and Non-Neutralization of HCV 1*a*/2*a* Chimeras by Monoclonal Antibodies.

The monoclonal antibodies that were capable of binding to the Peptide B region of the E2 protein were tested for their capacity to neutralize HCV infection in a cell culture system. A genotype 1*a*/2*a* chimeric HCV was used for the neutralization assay because the peptide sequence of the genotype 1*a* virus was used to design the immunogen for generating these monoclonal antibodies.

Each antibody (ascites fluid, 1:200) was incubated with appropriately diluted genotype 1*a*/2*a* virus, before adding the mixture to Huh 7.5 cells. Cell culture medium (DMEM) was used as a negative control for the antibody. The results are shown in FIG. 2A in which the x axis indicates the particular antibody tested in the experiment and the y axis indicates the relative infectivity of the virus (%), i.e., percent of the negative control. Each bar represents the mean of at least 3 independent experiments with the error bar showing the standard error of the mean indicated at the top of each bar.

As shown in FIG. 2A, antibodies #8 and #41 were able to neutralize the genotype 1*a*/2*a* virus. In contrast, antibodies #12 and #50, which also recognized Peptide B in an ELISA (FIG. 1C), were unable to neutralize the virus.

To ascertain whether the observed neutralization of the 1*a*/2*a* chimeric virus was Peptide B-specific, adsorption experiments were performed to deplete Peptide B-specific binding activity from the ascites fluid that contained neutralizing antibody #41. Antibody #41 was adsorbed with (+) or without (-) Peptide B prior to performing an ELISA to test its binding to Peptide B (left panel of FIG. 2B), and a neutralization assay to assess its neutralizing activity in Huh 7.5 cells (right panel of FIG. 2B). Each of the samples shown on the x axis was tested at a dilution of $1{:}10^5$ in an ELISA. The y axis indicates the absorbance at 405 nm obtained in an ELISA, representing the specific binding of a given antibody to Peptide B. The data shown represent at least 3 independent experiments. The standard deviation of the assay is indicated. For the neutralization assay (right panel), the supernatant was diluted at 1:400, and incubated with the genotype 1*a*/2*a* virus before adding the mixture to Huh 7.5 cells. The cell culture medium (Med) was used as the negative control against the tested antibodies. The x axis indicates the samples tested in this assay. The y axis indicates the relative infectivity of the virus (%), i.e., percent of the negative control. The statistical significance of the difference in infectivity is also indicated.

Figure 2B:
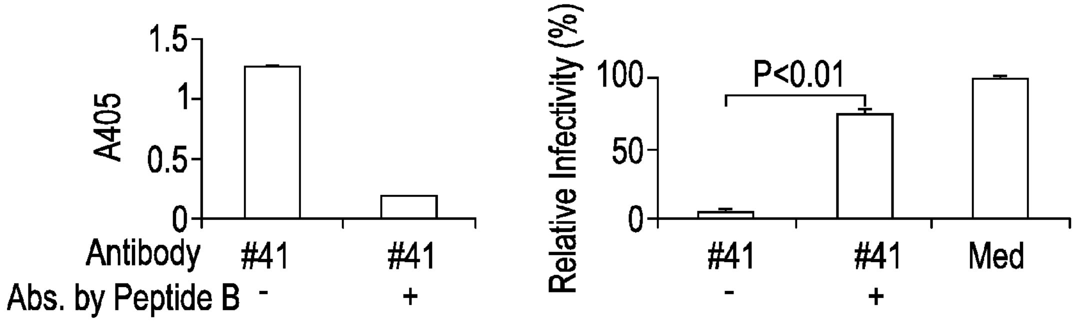

As demonstrated by the ELISA results shown in FIG. 2B (left panel), the Peptide B-specific binding activity could be substantially absorbed out by Peptide B. Concurrently, its neutralizing activity was also significantly diminished (FIG. 2B, right panel).

Figure 2C:
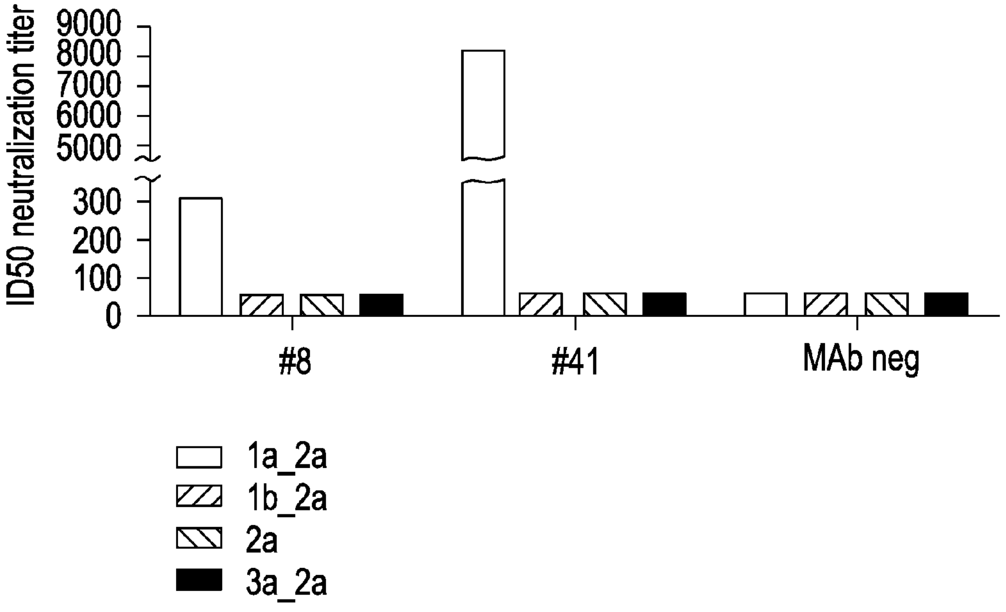

The two Peptide B-binding antibodies showing neutralization of genotype 1*a*/2*a* were tested for their ability to neutralize other genotypes. Serially diluted antibodies were tested against J6/JFH1, a genotype 2*a* virus, 1*a*/2*a,* 1*b*/2*a* and 3*a*/2*a* genotypes in Huh 7.5 cells with the same procedure described above. The results are shown in FIG. 2C. Neutralizing antibodies #8 and #41 were not able to neutralize the genotype 2*a* virus, J6/JFH1 (FIG. 2C), or other chimeric viruses 1*b*/2*a* and 3*a*/2*a.* These results demonstrated that antibodies #8 and #41, through the direct binding of Peptide B, could only neutralize HCV in a genotype 1*a* virus-specific manner.

Example 3

Figures 3, 4:
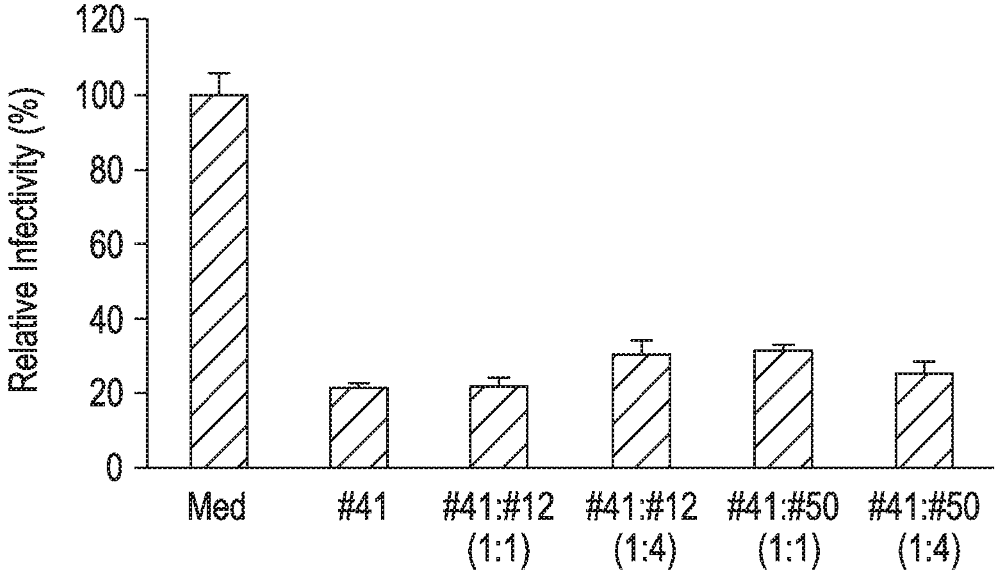
FIG. 3 presents a histogram showing the inability of non-neutralizing antibodies (#12 and #50) to block virus neutralization by antibody #41. Results from three independent experiments are shown with the error bar indicating the standard error of the mean.
FIG. 4 summarizes results of epitope mapping by screening random peptide phage-display libraries with the two neutralizing Peptide B-binding antibodies. The candidate core residues at the epitope-paratope contact interfaces are indicated in bold font. The symbol (x) denotes the amino acid residue other than L at the position. The peptide sequences, from top to bottom, are SEQ ID NOs:6-13, respectively.

Neutralization of HCV by Antibody #41 in the Presence or Absence of Non-Neutralizing Antibodies The ability of antibody #41 to neutralize genotype 1*a*/2*a* virus was measured in the presence or absence of non-neutralizing antibody #12 or #50. Neutralizing antibody #41 was diluted at 1:400 in DMEM, and then mixed with antibody #12 or #50 at ratios of 1:1 and 1:4 (v/v). The antibody mixture was subsequently incubated with genotype 1*a*/2*a* chimeric virus at 37° C. for 1 h before being added to Huh 7.5 cells. The results from 3 independent experiments are presented in FIG. 3. Neither antibody #12 nor #50 showed any interfering effect on the neutralizing ability of monoclonal antibody #41 (FIG. 3). Similar results were obtained in experiments with antibody #8.

Example 4

Residue-Specific Binding of Neutralizing and Non-Neutralizing Antibodies

The residues involved in the binding of the four Peptide B-binding antibodies were mapped by screening random peptide phage display libraries. The amino acid sequences of phage clusters identified after at least 3 rounds of screening phage-display libraries (12-mer and 7-mer) with neutralizing antibodies #8 and #41 are shown in FIG. 4 along with the number of specific peptides sequenced/the total number of peptides sequenced (shown in parenthesis).

To further determine the residue-specificity of these antibodies, each of the binding residues identified by the phage display analysis were substituted one at a time by an Alanine residue in a truncated version of Peptide B (" B short" ; a.a. 434-446 of SEQ ID NO:1) (see FIG. 5), and then tested by ELISA to determine the effect of the specific substitution on the binding of these antibodies. Biotin-conjugated peptides were chemically synthesized to represent B short and its mutations. The B short mutant peptides shown in FIG. 5 contained a single alanine (A) substitution at positions 437, 438, 440, 441 and 442, respectively.

Figures 5A, 5B:
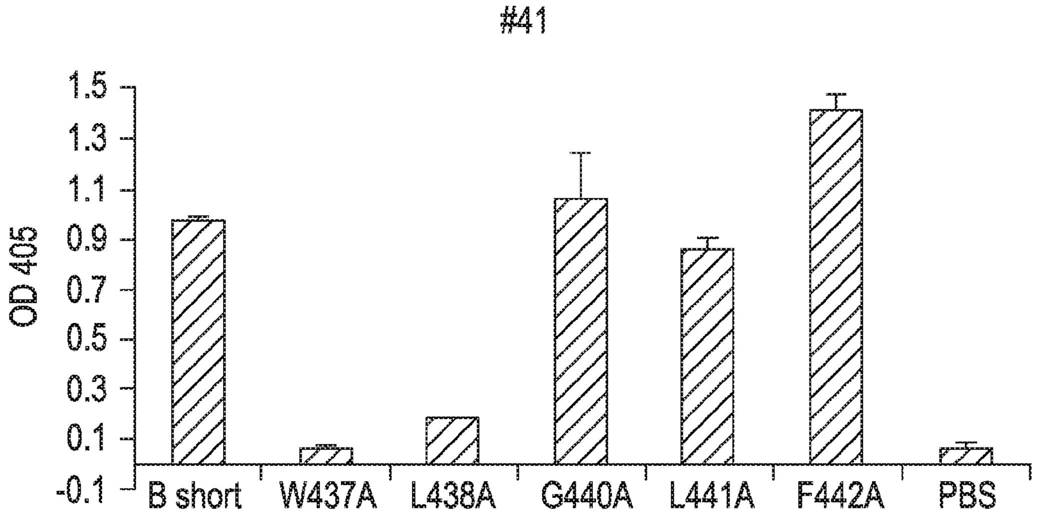
FIG. 5 presents identification of residues involved in antibody recognition by mutational analysis. Panel (A) indicates the mutated sequences chemically synthesized and tested by ELISA. The sequence of Peptide B short, is amino acids 434-446 of SEQ ID NO:1 and, as shown below the sequence, the B short mutant peptides contained a single alanine (A) substitution at positions 437, 438, 440, 441 and 442, respectively. A hyphen indicates an amino acid residue in the mutant peptides identical to that of the H77 sequence. Panel (B) is a histogram showing detection of antibody #41 binding by ELISA with the biotin-conjugated B short peptide and its mutants at 1:$10^5$ dilution, and applied as the primary antibody. PBS was included as the negative control. The x axis indicates the mutation used in each assay. The y axis indicates the absorbance at 405 nm, representing specific binding of the antibody to each individual peptide. Data shown represent 3 independent experiments with standard deviation indicated as error bars.

In the ELISA, biotin-conjugated B short peptide and its mutants were added to streptavidin-coated 96-well plates at 200 ng/well. The monoclonal antibody (ascites fluid) was diluted at $1:10^5$ dilution, and applied as the primary antibody. Phosphate buffered saline (PBS) was included as the negative control. The results of the ELISA using antibody #41 are shown in FIG. 5. Similar experiments were performed with neutralizing antibody #8 and nonneutralizing antibodies #12 and #50.

Residues determined to be involved in binding for each of the four antibodies are summarized in FIG. 6A.

All four antibodies tested in this study, irrespective of their neutralizing function, lost their binding to B short when W437 or L438 was replaced by an alanine residue, thus confirming that positions 437 and 438 were core contact residues recognized by these antibodies. Neutralizing antibodies #8 and #41 were less affected by the substitution at positions 441 and 442 in contrast to the effect on the binding capacities of the non-neutralizing antibodies #12 and #50.

Figures 7A, 7B:
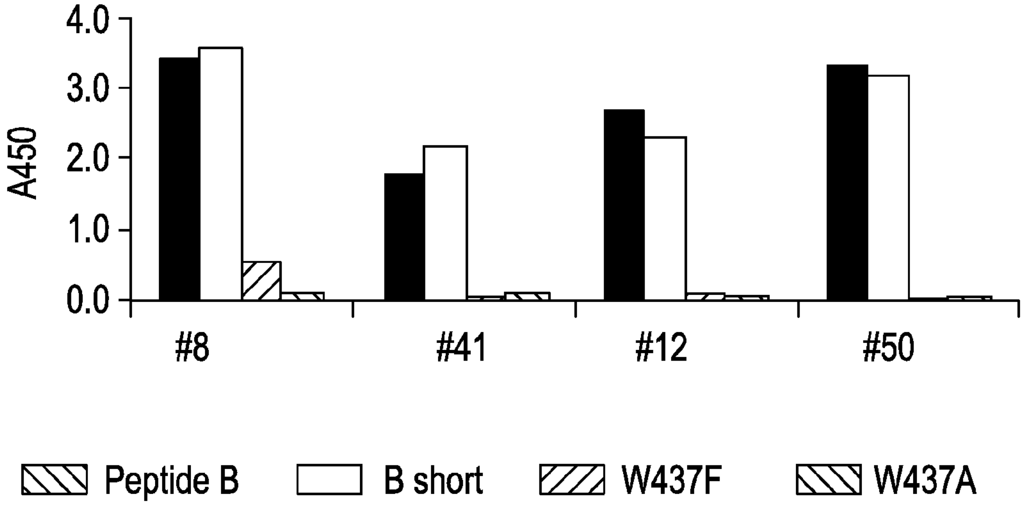
FIG. 7 shows the effect of the W437F switch on antibody binding. Panel (A) shows a schematic representation of the mutations of peptide B used in the ELISA. Biotin-conjugated peptides were chemically synthesized to represent Peptide B (residues 427-446 of SEQ ID NO:1), the truncated Peptide B (B short) (residues 434-446 of SEQ ID NO:1), and B short sequences with the indicated specific single mutations, F or A, at position 437. A hyphen indicates an amino acid residue identical to that of the H77 sequence. Panel (B) shows a histogram of results from the ELISA. The x axis indicates the antibodies used in this assay. The y axis indicates the absorbance obtained at 450 nm, which represents the measurement of specific binding of a given antibody to each individual peptide.

HCV genotype 1*a* has a W437 in its E2 protein, whereas the other HCV genotypes often contain an F residue at the same position (FIG. 6B). We hypothesized that the genotype 1*a*-specific neutralizing antibodies are limited to one genotype because of their inability to recognize F437. To test this hypothesis, we substituted the W residue at position 437 in the truncated Peptide B (B short) with an F residue and then evaluated its effect on binding in an ELISA experiment. The biotin-conjugated peptides chemically synthesized for this experiment to represent Peptide B (residues 427-446 of SEQ ID NO:1), the truncated Peptide B (B short) (residues 434-446 of SEQ ID NO:1), and B short sequences with the indicated specific single mutations at position 437 are shown in FIG. 7A. A hyphen indicates an amino acid residue identical to that of the H77 sequence.

Biotin-conjugated peptide B, B short peptide, or a B short mutans was added to streptavidin-coated 96-well plates at 200 ng/well. Each monoclonal antibody (ascites fluid) was used at a $1:10^5$ dilution as the primary antibody in the ELISA. Cell culture medium was used as the negative control of the antibody. The ELISA results are shown in FIG. 7B.

The W437F switch resulted in a loss of binding by neutralizing antibodies #41 and #8 to B short (FIG. 7B), as well as in non-neutralizing antibodies #12 and #50. This result confirmed that the presence of W437 was required for the shared recognition by these antibodies, and further indicated that W437 might be indispensable for the observed genotype 1*a*-specific neutralization of HCV shown by antibodies #41 and #8.

Example 5

Sequencing of Mouse Monoclonal Antibody (mAb) #41

About $5\times10^7$ of #41 hybridoma cells were used to extract the mRNA with Trizol and chloroform. Reverse transcriptase (RT) reaction was performed with SUPERSCRIPT® III First-Strand Synthesis Supermix Kit (Life Technologies) and multiple primers for the kappa and heavy chains, respectively. PCR was performed using multiple sets of primers for the kappa and heavy chains. The PCR amplification products were confirmed and purified using 1% agarose and then sequenced. Sequence results from multiple primers were aligned and analyzed using IMGT/V-QUEST (Brochet, X., et al. Nucl. Acids Res, 36, W503-508 (2008)), available on the internet from IIMGT®, the International ImMunoGeneTics Information System® Lefranc, M.-P., et al. Nucl. Acids Res, 37, D1006-D1012 (2009)). Nucleotide sequences of the heavy chain and the light (kappa) chain are SEQ ID NOS: 4 and 5, respectively. Translation of SEQ ID NOS: 4 and 5 yield protein sequences of the heavy chain and the light (kappa) chain of SEQ ID NOS: 2 and 3, respectively. FIG. 8 shows the nucleotide sequence and translated protein sequence of the kappa chain and the heavy chain of antibody #41.

The terms “a” and “an” do not denote a limitation of quantity, but rather denote the presence of at least one of the referenced item. The term “or” means “and/or” . The terms “comprising” , “having” , “including” , and “containing” are to be construed as open-ended terms (i.e., meaning “including, but not limited to”). The modifier “about” used in connection with a quantity is inclusive of the stated value and has the meaning dictated by the context (e.g., includes the degree of error associated with measurement of the particular quantity).

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

Unless defined otherwise, technical and scientific terms used herein have the same meaning as is commonly understood by one of skill in the art to which this invention belongs.

Embodiments of this invention are described herein, including the best mode known to the inventors for carrying out the invention. Variations of these embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated antibody or fragment thereof specifically binding to hepatitis C virus (HCV) E2 protein Epitope II, the antibody or fragment thereof comprising a heavy chain variable region comprising complementarity determining region (CDR) amino acid sequences CDR1 comprising residues 25-32 (GYSFTNYY) of SEQ ID NO:2, CDR2 comprising residues 50-57 (IFPGGGNT) of SEQ ID NO:2, and CDR3 comprising residues 96-107 (SRDIY GDAWFAY) of SEQ ID NO:2; and a light chain variable region comprising CDR amino acid sequences CDR1 comprising residues 27-37 (Q NIVHRNGNTY) of SEQ ID NO:3, CDR2 comprising residues 55-57 (KVS) of SEQ ID NO:3, and CDR3 comprising residues 94-102 (FQGS HFPPT) of SEQ ID NO:3.

2. The antibody or fragment thereof of claim 1, wherein the heavy chain variable region comprises the amino acid sequence of SEQ ID NO: 2, and the light chain variable region comprises the amino acid sequence of SEQ ID NO: 3.

3. The antibody or fragment thereof of claim 1 binding specifically to at least residues 434-446 of HCV E2 protein Epitope II (EP II), EPII comprising residues 427-446 of SEQ ID NO:1.

4. The isolated antibody or fragment thereof of claim 1, wherein the antibody is a monoclonal antibody.

5. The isolated antibody or fragment thereof of claim 1, wherein the antibody is a humanized antibody.

6. The isolated antibody or fragment thereof of claim 1, wherein the HCV E2 protein Epitope II (EP II) comprises $W^{437}$.

7. The isolated antibody or fragment thereof of claim 2, wherein the heavy chain variable region is encoded by SEQ ID NO:4.

8. The isolated antibody or fragment thereof of claim 2, wherein the light chain variable region is encoded by SEQ ID NO:5.

9. The antibody or fragment thereof of claim 1, wherein the antibody or fragment thereof neutralizes HCV genotype 1*a* in a cell culture system.

10. A composition comprising the antibody or fragment thereof of claim 1; and a pharmaceutically acceptable carrier.

11. A composition comprising the antibody or fragment thereof of claim 1, wherein the antibody or fragment thereof is linked to a toxic material, a chemotherapeutic agent, or a labeling material.

12. A method of detecting hepatitis C virus (HCV) E2 protein Epitope II in a sample comprising contacting the antibody of claim 1 with a sample under conditions such that the antibody binds an HCV E2 protein Epitope II (EP II) sequence comprising at least residues 427-446 of SEQ ID NO:1; and detecting antibody bound to EP II.

13. A method of treating or preventing HCV infection comprising administering the antibody or fragment thereof according to claim 1 to a subject exposed to or infected with HCV.

14. The method of claim 13, wherein the subject is a liver transplant patient.

* * * * *

SEQUENCE LISTING

```
<160> NUMBER OF SEQ ID NOS: 13

<210> SEQ ID NO 1
<211> LENGTH: 3011
<212> TYPE: PRT
<213> ORGANISM: Hepatitis C virus

<400> SEQUENCE: 1

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240
```

-continued

```
Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Ser Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655
```

-continued

```
Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
    690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
                725                 730                 735

Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
        755                 760                 765

Leu Val Phe Phe Cys Phe Ala Trp Tyr Leu Lys Gly Arg Trp Val Pro
    770                 775                 780

Gly Ala Val Tyr Ala Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
                805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Met Trp Trp Leu Gln Tyr
        835                 840                 845

Phe Leu Thr Arg Val Glu Ala Gln Leu His Val Trp Val Pro Pro Leu
    850                 855                 860

Asn Val Arg Gly Gly Arg Asp Ala Val Ile Leu Leu Met Cys Val Val
865                 870                 875                 880

His Pro Thr Leu Val Phe Asp Ile Thr Lys Leu Leu Leu Ala Ile Phe
                885                 890                 895

Gly Pro Leu Trp Ile Leu Gln Ala Ser Leu Leu Lys Val Pro Tyr Phe
            900                 905                 910

Val Arg Val Gln Gly Leu Leu Arg Ile Cys Ala Leu Ala Arg Lys Ile
        915                 920                 925

Ala Gly Gly His Tyr Val Gln Met Ala Ile Ile Lys Leu Gly Ala Leu
    930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
                965                 970                 975

Ser Arg Met Glu Thr Lys Leu Ile Thr Trp Gly Ala Asp Thr Ala Ala
            980                 985                 990

Cys Gly Asp Ile Ile Asn Gly Leu  Pro Val Ser Ala Arg  Arg Gly Gln
        995                 1000                 1005

Glu Ile  Leu Leu Gly Pro Ala  Asp Gly Met Val Ser  Lys Gly Trp
    1010                 1015                 1020

Arg Leu  Leu Ala Pro Ile Thr  Ala Tyr Ala Gln Gln  Thr Arg Gly
    1025                 1030                 1035

Leu Leu  Gly Cys Ile Ile Thr  Ser Leu Thr Gly Arg  Asp Lys Asn
    1040                 1045                 1050

Gln Val  Glu Gly Glu Val Gln  Ile Val Ser Thr Ala  Thr Gln Thr
    1055                 1060                 1065

Phe Leu  Ala Thr Cys Ile Asn  Gly Val Cys Trp Thr  Val Tyr His
```

```
    1070                1075                1080

Gly Ala  Gly Thr Arg Thr Ile  Ala Ser Pro Lys Gly  Pro Val Ile
    1085                1090                1095

Gln Met  Tyr Thr Asn Val Asp  Gln Asp Leu Val Gly  Trp Pro Ala
    1100                1105                1110

Pro Gln  Gly Ser Arg Ser Leu  Thr Pro Cys Thr Cys  Gly Ser Ser
    1115                1120                1125

Asp Leu  Tyr Leu Val Thr Arg  His Ala Asp Val Ile  Pro Val Arg
    1130                1135                1140

Arg Arg  Gly Asp Ser Arg Gly  Ser Leu Leu Ser Pro  Arg Pro Ile
    1145                1150                1155

Ser Tyr  Leu Lys Gly Ser Ser  Gly Gly Pro Leu Leu  Cys Pro Ala
    1160                1165                1170

Gly His  Ala Val Gly Leu Phe  Arg Ala Ala Val Cys  Thr Arg Gly
    1175                1180                1185

Val Ala  Lys Ala Val Asp Phe  Ile Pro Val Glu Asn  Leu Glu Thr
    1190                1195                1200

Thr Met  Arg Ser Pro Val Phe  Thr Asp Asn Ser Ser  Pro Pro Ala
    1205                1210                1215

Val Pro  Gln Ser Phe Gln Val  Ala His Leu His Ala  Pro Thr Gly
    1220                1225                1230

Ser Gly  Lys Ser Thr Lys Val  Pro Ala Ala Tyr Ala  Ala Gln Gly
    1235                1240                1245

Tyr Lys  Val Leu Val Leu Asn  Pro Ser Val Ala Ala  Thr Leu Gly
    1250                1255                1260

Phe Gly  Ala Tyr Met Ser Lys  Ala His Gly Val Asp  Pro Asn Ile
    1265                1270                1275

Arg Thr  Gly Val Arg Thr Ile  Thr Thr Gly Ser Pro  Ile Thr Tyr
    1280                1285                1290

Ser Thr  Tyr Gly Lys Phe Leu  Ala Asp Gly Gly Cys  Ser Gly Gly
    1295                1300                1305

Ala Tyr  Asp Ile Ile Ile Cys  Asp Glu Cys His Ser  Thr Asp Ala
    1310                1315                1320

Thr Ser  Ile Leu Gly Ile Gly  Thr Val Leu Asp Gln  Ala Glu Thr
    1325                1330                1335

Ala Gly  Ala Arg Leu Val Val  Leu Ala Thr Ala Thr  Pro Pro Gly
    1340                1345                1350

Ser Val  Thr Val Ser His Pro  Asn Ile Glu Glu Val  Ala Leu Ser
    1355                1360                1365

Thr Thr  Gly Glu Ile Pro Phe  Tyr Gly Lys Ala Ile  Pro Leu Glu
    1370                1375                1380

Val Ile  Lys Gly Gly Arg His  Leu Ile Phe Cys His  Ser Lys Lys
    1385                1390                1395

Lys Cys  Asp Glu Leu Ala Ala  Lys Leu Val Ala Leu  Gly Ile Asn
    1400                1405                1410

Ala Val  Ala Tyr Tyr Arg Gly  Leu Asp Val Ser Val  Ile Pro Thr
    1415                1420                1425

Ser Gly  Asp Val Val Val Val  Ser Thr Asp Ala Leu  Met Thr Gly
    1430                1435                1440

Phe Thr  Gly Asp Phe Asp Ser  Val Ile Asp Cys Asn  Thr Cys Val
    1445                1450                1455

Thr Gln  Thr Val Asp Phe Ser  Leu Asp Pro Thr Phe  Thr Ile Glu
    1460                1465                1470
```

-continued

```
Thr Thr  Thr Leu Pro Gln Asp  Ala Val Ser Arg Thr  Gln Arg Arg
    1475                 1480                 1485

Gly Arg  Thr Gly Arg Gly Lys  Pro Gly Ile Tyr Arg  Phe Val Ala
    1490                 1495                 1500

Pro Gly  Glu Arg Pro Ser Gly  Met Phe Asp Ser Ser  Val Leu Cys
    1505                 1510                 1515

Glu Cys  Tyr Asp Ala Gly Cys  Ala Trp Tyr Glu Leu  Thr Pro Ala
    1520                 1525                 1530

Glu Thr  Thr Val Arg Leu Arg  Ala Tyr Met Asn Thr  Pro Gly Leu
    1535                 1540                 1545

Pro Val  Cys Gln Asp His Leu  Glu Phe Trp Glu Gly  Val Phe Thr
    1550                 1555                 1560

Gly Leu  Thr His Ile Asp Ala  His Phe Leu Ser Gln  Thr Lys Gln
    1565                 1570                 1575

Ser Gly  Glu Asn Phe Pro Tyr  Leu Val Ala Tyr Gln  Ala Thr Val
    1580                 1585                 1590

Cys Ala  Arg Ala Gln Ala Pro  Pro Pro Ser Trp Asp  Gln Met Trp
    1595                 1600                 1605

Lys Cys  Leu Ile Arg Leu Lys  Pro Thr Leu His Gly  Pro Thr Pro
    1610                 1615                 1620

Leu Leu  Tyr Arg Leu Gly Ala  Val Gln Asn Glu Val  Thr Leu Thr
    1625                 1630                 1635

His Pro  Ile Thr Lys Tyr Ile  Met Thr Cys Met Ser  Ala Asp Leu
    1640                 1645                 1650

Glu Val  Val Thr Ser Thr Trp  Val Leu Val Gly Gly  Val Leu Ala
    1655                 1660                 1665

Ala Leu  Ala Ala Tyr Cys Leu  Ser Thr Gly Cys Val  Val Ile Val
    1670                 1675                 1680

Gly Arg  Ile Val Leu Ser Gly  Lys Pro Ala Ile Ile  Pro Asp Arg
    1685                 1690                 1695

Glu Val  Leu Tyr Gln Glu Phe  Asp Glu Met Glu Glu  Cys Ser Gln
    1700                 1705                 1710

His Leu  Pro Tyr Ile Glu Gln  Gly Met Met Leu Ala  Glu Gln Phe
    1715                 1720                 1725

Lys Gln  Lys Ala Leu Gly Leu  Leu Gln Thr Ala Ser  Arg Gln Ala
    1730                 1735                 1740

Glu Val  Ile Thr Pro Ala Val  Gln Thr Asn Trp Gln  Lys Leu Glu
    1745                 1750                 1755

Val Phe  Trp Ala Lys His Met  Trp Asn Phe Ile Ser  Gly Ile Gln
    1760                 1765                 1770

Tyr Leu  Ala Gly Leu Ser Thr  Leu Pro Gly Asn Pro  Ala Ile Ala
    1775                 1780                 1785

Ser Leu  Met Ala Phe Thr Ala  Ala Val Thr Ser Pro  Leu Thr Thr
    1790                 1795                 1800

Gly Gln  Thr Leu Leu Phe Asn  Ile Leu Gly Gly Trp  Val Ala Ala
    1805                 1810                 1815

Gln Leu  Ala Ala Pro Gly Ala  Ala Thr Ala Phe Val  Gly Ala Gly
    1820                 1825                 1830

Leu Ala  Gly Ala Ala Ile Gly  Ser Val Gly Leu Gly  Lys Val Leu
    1835                 1840                 1845

Val Asp  Ile Leu Ala Gly Tyr  Gly Ala Gly Val Ala  Gly Ala Leu
    1850                 1855                 1860
```

```
Val Ala  Phe Lys Ile Met Ser  Gly Glu Val Pro Ser  Thr Glu Asp
    1865                 1870                 1875

Leu Val  Asn Leu Leu Pro Ala  Ile Leu Ser Pro Gly  Ala Leu Val
    1880                 1885                 1890

Val Gly  Val Val Cys Ala Ala  Ile Leu Arg Arg His  Val Gly Pro
    1895                 1900                 1905

Gly Glu  Gly Ala Val Gln Trp  Met Asn Arg Leu Ile  Ala Phe Ala
    1910                 1915                 1920

Ser Arg  Gly Asn His Val Ser  Pro Thr His Tyr Val  Pro Glu Ser
    1925                 1930                 1935

Asp Ala  Ala Ala Arg Val Thr  Ala Ile Leu Ser Ser  Leu Thr Val
    1940                 1945                 1950

Thr Gln  Leu Leu Arg Arg Leu  His Gln Trp Ile Ser  Ser Glu Cys
    1955                 1960                 1965

Thr Thr  Pro Cys Ser Gly Ser  Trp Leu Arg Asp Ile  Trp Asp Trp
    1970                 1975                 1980

Ile Cys  Glu Val Leu Ser Asp  Phe Lys Thr Trp Leu  Lys Ala Lys
    1985                 1990                 1995

Leu Met  Pro Gln Leu Pro Gly  Ile Pro Phe Val Ser  Cys Gln Arg
    2000                 2005                 2010

Gly Tyr  Arg Gly Val Trp Arg  Gly Asp Gly Ile Met  His Thr Arg
    2015                 2020                 2025

Cys His  Cys Gly Ala Glu Ile  Thr Gly His Val Lys  Asn Gly Thr
    2030                 2035                 2040

Met Arg  Ile Val Gly Pro Arg  Thr Cys Arg Asn Met  Trp Ser Gly
    2045                 2050                 2055

Thr Phe  Pro Ile Asn Ala Tyr  Thr Thr Gly Pro Cys  Thr Pro Leu
    2060                 2065                 2070

Pro Ala  Pro Asn Tyr Lys Phe  Ala Leu Trp Arg Val  Ser Ala Glu
    2075                 2080                 2085

Glu Tyr  Val Glu Ile Arg Arg  Val Gly Asp Phe His  Tyr Val Ser
    2090                 2095                 2100

Gly Met  Thr Thr Asp Asn Leu  Lys Cys Pro Cys Gln  Ile Pro Ser
    2105                 2110                 2115

Pro Glu  Phe Phe Thr Glu Leu  Asp Gly Val Arg Leu  His Arg Phe
    2120                 2125                 2130

Ala Pro  Pro Cys Lys Pro Leu  Leu Arg Glu Glu Val  Ser Phe Arg
    2135                 2140                 2145

Val Gly  Leu His Glu Tyr Pro  Val Gly Ser Gln Leu  Pro Cys Glu
    2150                 2155                 2160

Pro Glu  Pro Asp Val Ala Val  Leu Thr Ser Met Leu  Thr Asp Pro
    2165                 2170                 2175

Ser His  Ile Thr Ala Glu Ala  Ala Gly Arg Arg Leu  Ala Arg Gly
    2180                 2185                 2190

Ser Pro  Pro Ser Met Ala Ser  Ser Ser Ala Ser Gln  Leu Ser Ala
    2195                 2200                 2205

Pro Ser  Leu Lys Ala Thr Cys  Thr Ala Asn His Asp  Ser Pro Asp
    2210                 2215                 2220

Ala Glu  Leu Ile Glu Ala Asn  Leu Leu Trp Arg Gln  Glu Met Gly
    2225                 2230                 2235

Gly Asn  Ile Thr Arg Val Glu  Ser Glu Asn Lys Val  Val Ile Leu
    2240                 2245                 2250

Asp Ser  Phe Asp Pro Leu Val  Ala Glu Glu Asp Glu  Arg Glu Val
```

```
    2255                2260                2265

Ser Val  Pro Ala Glu Ile Leu  Arg Lys Ser Arg Arg  Phe Ala Arg
    2270                2275                2280

Ala Leu  Pro Val Trp Ala Arg  Pro Asp Tyr Asn Pro  Pro Leu Val
    2285                2290                2295

Glu Thr  Trp Lys Lys Pro Asp  Tyr Glu Pro Pro Val  Val His Gly
    2300                2305                2310

Cys Pro  Leu Pro Pro Pro Arg  Ser Pro Pro Val Pro  Pro Pro Arg
    2315                2320                2325

Lys Lys  Arg Thr Val Val Leu  Thr Glu Ser Thr Leu  Ser Thr Ala
    2330                2335                2340

Leu Ala  Glu Leu Ala Thr Lys  Ser Phe Gly Ser Ser  Ser Thr Ser
    2345                2350                2355

Gly Ile  Thr Gly Asp Asn Thr  Thr Thr Ser Ser Glu  Pro Ala Pro
    2360                2365                2370

Ser Gly  Cys Pro Pro Asp Ser  Asp Val Glu Ser Tyr  Ser Ser Met
    2375                2380                2385

Pro Pro  Leu Glu Gly Glu Pro  Gly Asp Pro Asp Leu  Ser Asp Gly
    2390                2395                2400

Ser Trp  Ser Thr Val Ser Ser  Gly Ala Asp Thr Glu  Asp Val Val
    2405                2410                2415

Cys Cys  Ser Met Ser Tyr Ser  Trp Thr Gly Ala Leu  Val Thr Pro
    2420                2425                2430

Cys Ala  Ala Glu Glu Gln Lys  Leu Pro Ile Asn Ala  Leu Ser Asn
    2435                2440                2445

Ser Leu  Leu Arg His His Asn  Leu Val Tyr Ser Thr  Thr Ser Arg
    2450                2455                2460

Ser Ala  Cys Gln Arg Gln Lys  Lys Val Thr Phe Asp  Arg Leu Gln
    2465                2470                2475

Val Leu  Asp Ser His Tyr Gln  Asp Val Leu Lys Glu  Val Lys Ala
    2480                2485                2490

Ala Ala  Ser Lys Val Lys Ala  Asn Leu Leu Ser Val  Glu Glu Ala
    2495                2500                2505

Cys Ser  Leu Thr Pro Pro His  Ser Ala Lys Ser Lys  Phe Gly Tyr
    2510                2515                2520

Gly Ala  Lys Asp Val Arg Cys  His Ala Arg Lys Ala  Val Ala His
    2525                2530                2535

Ile Asn  Ser Val Trp Lys Asp  Leu Leu Glu Asp Ser  Val Thr Pro
    2540                2545                2550

Ile Asp  Thr Thr Ile Met Ala  Lys Asn Glu Val Phe  Cys Val Gln
    2555                2560                2565

Pro Glu  Lys Gly Gly Arg Lys  Pro Ala Arg Leu Ile  Val Phe Pro
    2570                2575                2580

Asp Leu  Gly Val Arg Val Cys  Glu Lys Met Ala Leu  Tyr Asp Val
    2585                2590                2595

Val Ser  Lys Leu Pro Leu Ala  Val Met Gly Ser Ser  Tyr Gly Phe
    2600                2605                2610

Gln Tyr  Ser Pro Gly Gln Arg  Val Glu Phe Leu Val  Gln Ala Trp
    2615                2620                2625

Lys Ser  Lys Lys Thr Pro Met  Gly Phe Ser Tyr Asp  Thr Arg Cys
    2630                2635                2640

Phe Asp  Ser Thr Val Thr Glu  Ser Asp Ile Arg Thr  Glu Glu Ala
    2645                2650                2655
```

```
Ile Tyr Gln Cys Cys Asp Leu Asp Pro Gln Ala Arg Val Ala Ile
    2660                2665                2670

Lys Ser Leu Thr Glu Arg Leu Tyr Val Gly Gly Pro Leu Thr Asn
    2675                2680                2685

Ser Arg Gly Glu Asn Cys Gly Tyr Arg Arg Cys Arg Ala Ser Gly
    2690                2695                2700

Val Leu Thr Thr Ser Cys Gly Asn Thr Leu Thr Cys Tyr Ile Lys
    2705                2710                2715

Ala Arg Ala Ala Cys Arg Ala Ala Gly Leu Gln Asp Cys Thr Met
    2720                2725                2730

Leu Val Cys Gly Asp Asp Leu Val Val Ile Cys Glu Ser Ala Gly
    2735                2740                2745

Val Gln Glu Asp Ala Ala Ser Leu Arg Ala Phe Thr Glu Ala Met
    2750                2755                2760

Thr Arg Tyr Ser Ala Pro Pro Gly Asp Pro Pro Gln Pro Glu Tyr
    2765                2770                2775

Asp Leu Glu Leu Ile Thr Ser Cys Ser Ser Asn Val Ser Val Ala
    2780                2785                2790

His Asp Gly Ala Gly Lys Arg Val Tyr Tyr Leu Thr Arg Asp Pro
    2795                2800                2805

Thr Thr Pro Leu Ala Arg Ala Ala Trp Glu Thr Ala Arg His Thr
    2810                2815                2820

Pro Val Asn Ser Trp Leu Gly Asn Ile Ile Met Phe Ala Pro Thr
    2825                2830                2835

Leu Trp Ala Arg Met Ile Leu Met Thr His Phe Phe Ser Val Leu
    2840                2845                2850

Ile Ala Arg Asp Gln Leu Glu Gln Ala Leu Asn Cys Glu Ile Tyr
    2855                2860                2865

Gly Ala Cys Tyr Ser Ile Glu Pro Leu Asp Leu Pro Pro Ile Ile
    2870                2875                2880

Gln Arg Leu His Gly Leu Ser Ala Phe Ser Leu His Ser Tyr Ser
    2885                2890                2895

Pro Gly Glu Ile Asn Arg Val Ala Ala Cys Leu Arg Lys Leu Gly
    2900                2905                2910

Val Pro Pro Leu Arg Ala Trp Arg His Arg Ala Arg Ser Val Arg
    2915                2920                2925

Ala Arg Leu Leu Ser Arg Gly Gly Arg Ala Ala Ile Cys Gly Lys
    2930                2935                2940

Tyr Leu Phe Asn Trp Ala Val Arg Thr Lys Leu Lys Leu Thr Pro
    2945                2950                2955

Ile Ala Ala Ala Gly Arg Leu Asp Leu Ser Gly Trp Phe Thr Ala
    2960                2965                2970

Gly Tyr Ser Gly Gly Asp Ile Tyr His Ser Val Ser His Ala Arg
    2975                2980                2985

Pro Arg Trp Phe Trp Phe Cys Leu Leu Leu Leu Ala Ala Gly Val
    2990                2995                3000

Gly Ile Tyr Leu Leu Pro Asn Arg
    3005                3010
```

<210> SEQ ID NO 2
<211> LENGTH: 107
<212> TYPE: PRT
<213> ORGANISM: Mus musculus

<400> SEQUENCE: 2

Val Lys Leu Gln Glu Ser Gly Pro Glu Leu Val Lys Pro Gly Ala Ser
1               5                   10                  15

Val Lys Ile Ser Cys Lys Ala Ser Gly Tyr Ser Phe Thr Asn Tyr Tyr
            20                  25                  30

Ile Asn Trp Val Lys Gln Arg Pro Gly Gln Gly Leu Glu Trp Ile Gly
        35                  40                  45

Trp Ile Phe Pro Gly Gly Gly Asn Thr Lys Tyr Ser Glu Lys Phe Lys
    50                  55                  60

Asp Lys Ala Thr Val Thr Ala Asp Thr Ser Ser Ser Thr Ala Tyr Met
65                  70                  75                  80

Gln Leu Ser Gly Leu Thr Ser Glu Asp Ser Ala Val Tyr Phe Cys Ser
                85                  90                  95

Arg Asp Ile Tyr Gly Asp Ala Trp Phe Ala Tyr
            100                 105

<210> SEQ ID NO 3
<211> LENGTH: 102
<212> TYPE: PRT
<213> ORGANISM: Mus musculus

<400> SEQUENCE: 3

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Arg
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Phe Pro Pro Thr
            100

<210> SEQ ID NO 4
<211> LENGTH: 324
<212> TYPE: DNA
<213> ORGANISM: Mus musculus

<400> SEQUENCE: 4
taggtgaagc tgcaggagtc aggacctgag ctggtgaagc ctggggcttc agtgaagata 60
tcctgcaagg cttctggcta cagtttcaca aactactata taaattgggt gaagcagagg 120
cctggacagg gacttgagtg gattggatgg atttttcctg gaggtggtaa tactaagtac 180
agtgagaagt tcaaggacaa ggccacagtc acggcagaca catcctccag cacagcctac 240
atgcagctca gcggcctgac atctgaggac tctgcagtct atttctgttc aagagacatc 300
tatggtgacg cctggtttgc ttac 324

<210> SEQ ID NO 5
<211> LENGTH: 306
<212> TYPE: DNA
<213> ORGANISM: Mus musculus

<400> SEQUENCE: 5

```
gatgttgtga tgacccaaac tccactctcc ctgcctgtca gtcttggaga tcaagcctcc     60

atctcttgca gatctagtca gaacattgta catagaaatg gaaacaccta tttagaatgg    120

tacctgcaga aaccaggcca gtctccaaag ctcctgatct acaaagtttc caaccgattt    180

tctggggtcc cagacaggtt cagtggcagt ggatcaggga cagatttcac actcaagatc    240

agcagagtgg aggctgagga tctgggactt tattactgct ttcaaggttc acattttcct    300

cccacg                                                               306
```

```
<210> SEQ ID NO 6
<211> LENGTH: 7
<212> TYPE: PRT
<213> ORGANISM: Artificial Sequence
<220> FEATURE:
<223> OTHER INFORMATION: SEQUENCE FROM PEPTIDE PHAGE DISPLAY LIBRARY

<400> SEQUENCE: 6

Thr Trp Leu Asn Met Phe Ser
1               5


<210> SEQ ID NO 7
<211> LENGTH: 7
<212> TYPE: PRT
<213> ORGANISM: Artificial Sequence
<220> FEATURE:
<223> OTHER INFORMATION: SEQUENCE FROM PEPTIDE PHAGE DISPLAY LIBRARY

<400> SEQUENCE: 7

Ser Trp Leu Asp Phe Thr His
1               5


<210> SEQ ID NO 8
<211> LENGTH: 12
<212> TYPE: PRT
<213> ORGANISM: Artificial Sequence
<220> FEATURE:
<223> OTHER INFORMATION: SEQUENCE FROM PEPTIDE PHAGE DISPLAY LIBRARY

<400> SEQUENCE: 8

Ala Gly Pro Asp Ser Trp Leu Gln Trp Leu Ala Gln
1               5                   10


<210> SEQ ID NO 9
<211> LENGTH: 12
<212> TYPE: PRT
<213> ORGANISM: Artificial Sequence
<220> FEATURE:
<223> OTHER INFORMATION: SEQUENCE FROM PEPTIDE PHAGE DISPLAY LIBRARY

<400> SEQUENCE: 9

Ile Thr Arg His Ser Gln Glu Trp Leu Leu Glu Ile
1               5                   10


<210> SEQ ID NO 10
<211> LENGTH: 12
<212> TYPE: PRT
<213> ORGANISM: Artificial Sequence
<220> FEATURE:
<223> OTHER INFORMATION: SEQUENCE FROM PEPTIDE PHAGE DISPLAY LIBRARY

<400> SEQUENCE: 10

Asn Gly Trp Leu Met Gln Asn Thr Leu Glu Pro Leu
1               5                   10
```

-continued

```
<210> SEQ ID NO 11
<211> LENGTH: 12
<212> TYPE: PRT
<213> ORGANISM: Artificial Sequence
<220> FEATURE:
<223> OTHER INFORMATION: SEQUENCE FROM PEPTIDE PHAGE DISPLAY LIBRARY

<400> SEQUENCE: 11

Ser Gln Asn Trp Leu Ser Asn Met Phe Ser Tyr Ser
1               5                   10


<210> SEQ ID NO 12
<211> LENGTH: 7
<212> TYPE: PRT
<213> ORGANISM: Artificial Sequence
<220> FEATURE:
<223> OTHER INFORMATION: SEQUENCE FROM PEPTIDE PHAGE DISPLAY LIBRARY

<400> SEQUENCE: 12

Trp Pro Ser Pro Leu Tyr Glu
1               5


<210> SEQ ID NO 13
<211> LENGTH: 12
<212> TYPE: PRT
<213> ORGANISM: Artificial Sequence
<220> FEATURE:
<223> OTHER INFORMATION: SEQUENCE FROM PEPTIDE PHAGE DISPLAY LIBRARY

<400> SEQUENCE: 13

Trp Pro Thr Leu Leu Tyr Glu Gly Pro Val Ile Arg
1               5                   10
```